(12) United States Patent
Xu et al.

(10) Patent No.: US 10,987,395 B2
(45) Date of Patent: Apr. 27, 2021

(54) *PALIURUS RAMOSISSIMUS* (LOUR.) POIR. EXTRACT AND PREPARATION METHODS AND USES THEREOF

(71) Applicant: Sichuan Academy of Chinese Medicine Sciences, Sichuan (CN)

(72) Inventors: Chaoqun Xu, Sichuan (CN); Dongxiao Li, Sichuan (CN); Guangming Shu, Sichuan (CN); Jia Ruan, Sichuan (CN); Yan Zhan, Sichuan (CN); Lei Tan, Sichuan (CN)

(73) Assignee: SICHUAN ACADEMY OF CHINESE MEDICINE SCIENCES, Sichuan (CN)

( * ) Notice: Subject to any disclaimer, the term of this patent is extended or adjusted under 35 U.S.C. 154(b) by 256 days.

(21) Appl. No.: 16/220,229

(22) Filed: Dec. 14, 2018

(65) Prior Publication Data
US 2019/0117718 A1    Apr. 25, 2019

Related U.S. Application Data

(62) Division of application No. 15/033,386, filed as application No. PCT/CN2014/089895 on Oct. 30, 2014, now abandoned.

(30) Foreign Application Priority Data

| Oct. 31, 2013 | (CN) | 201310528511.6 |
| Jan. 15, 2014 | (CN) | 201410018576.0 |
| Jan. 15, 2014 | (CN) | 201410019123.X |
| Jan. 17, 2014 | (CN) | 201410023850.3 |
| Jan. 23, 2014 | (CN) | 201410030860.X |
| Jan. 23, 2014 | (CN) | 201410032900.4 |

(51) Int. Cl.
*A61K 36/72* (2006.01)

(52) U.S. Cl.
CPC .......... *A61K 36/72* (2013.01); *A61K 2236/33* (2013.01); *A61K 2236/35* (2013.01)

(58) Field of Classification Search
None
See application file for complete search history.

(56) References Cited

FOREIGN PATENT DOCUMENTS

| CN | 1383878 A | * 12/2002 |
| CN | 1814067 A | 8/2006 |
| CN | 101181609 A | * 5/2008 |
| CN | 101181609 A | 5/2008 |
| CN | 101376870 A | 3/2009 |
| CN | 102276670 A | 12/2011 |
| CN | 103550323 A | 2/2014 |
| CN | 103735653 A | 4/2014 |
| CN | 103735654 A | 4/2014 |
| CN | 103751315 A | 4/2014 |
| CN | 103751316 A | 4/2014 |
| CN | 103800466 A | 5/2014 |

OTHER PUBLICATIONS

Wei, Guofeng et al., "The Antitussive and Expectorant Effect of Paliurus Ramosissimus Pair and the Extraction and Separation of its Chemical Component", Journal of Youjiang Medical College for Nationalities, Apr. 30, 1998, No. 2, pp. 176 and 177.
Yu, Lei et al., "Studies on Chemical Constituents From Fruits of Paliurus Ramosissimus", China Journal of Chinese \lateria Medica, Dec. 31, 2006, vol. 31, No. 24, pp. 2049 to 2052.
International Search Report issued in corresponding International Application No. PCT/CN2014/089895, dated Jan. 9, 2015, 4 pages.
Guofeng, W., et al., "The Antitussive and Expectorant Effect of Paliurus Ramosissimus Poir and the Extraction and Separation of its Chemical Component", Youjiang Medical College for National Minorities, Bose, Guangxi, P.R. China 533000, China Academic Journal Electronic Publishing House, 1998, p. 177.
Yu, L., et al., "Studies on Chemical Constituents from Fruits of Paliurus Ramosissimus", Key Laboratory of Bioactive Substances and Resources Utilization of Chinese Herbal Medicine, Ministry of Education, Institute of Materia Medica, Chinese Academy of Medical Sciences and Peking Union Medical College, Beijing 100050, China, vol. 31, Issue 24, Dec. 2006, pp. 2051-2052.
Yu (China Journal of Chinese Materia Medica, (Dec. 2006) vol. 31, No. 24, pp. 2049-2052—English translation).

* cited by examiner

*Primary Examiner* — Susan Hoffman
(74) *Attorney, Agent, or Firm* — Burns & Levinson LLP; Christopher R. Cowles

(57) ABSTRACT

The invention belongs to the field of medicine, involving new uses of *Paliurus ramosissimus* (Lour.) Poir. and its extract, in particular the use of *Paliurus ramosissimus* (Lour.) Poir. and its extract in preparation of drugs with anti-fibrotic, anti-fungal, and anti-tumor activities, for the treatment of oral and digestive tract inflammation or (and) ulcer-related diseases, or with bi-directional immunomodulatory effects.

2 Claims, No Drawings

PALIURUS RAMOSISSIMUS (LOUR.) POIR. EXTRACT AND PREPARATION METHODS AND USES THEREOF

RELATED APPLICATION

This application is a divisional of U.S. application Ser. No. 15/033,386, now abandoned, which is the U.S. national stage pursuant to 35 U.S.C. § 371, of United States international application Ser. No. PCT/CN2014/089895 filed Oct. 30, 2014 and published in Chinese on May 7, 2015 as publication WO2015/062517A1, which claims the benefit of Chinese application No. 201310528511.6, filed on Oct. 31, 2013, Chinese application No. 201410018576.0, filed Jan. 15, 2014, Chinese application No. 201410019123.X, filed Jan. 15, 2014, Chinese application No. 201410023850.3, filed on Jan. 17, 2014, Chinese application No. 201410030860.X, filed Jan. 23, 2014 and Chinese application No. 201410032900.4, filed Jan. 23, 2014. The entire contents of the aforementioned patent applications are incorporated herein by this reference.

TECHNICAL FIELD

The invention belongs to the field of medicine, in particular to the *Paliurus ramosissimus* (Lour.) Poir. extract and its preparation methods and uses.

BACKGROUND TECHNIQUE

*Paliurus ramosissimus* (Lour.) Poir., a deciduous shrub, is a common medicinal plant. It has been reported that its branches, leaves, roots and fruits can be used as medicine. It is bitter, flat, and non-toxic. It can remove cold and promote blood circulation, reduce swelling, act as antipyretic, treat bruises and injuries, and relieve heart and abdomen pains. It is included in the "Chinese Traditional Medicine Dictionary" and some local drug records.

During study, the inventors of the present invention have identified that *Paliurus ramosissimus* (Lour.) Poir. and its extract have good anti-fibrotic, anti-fungal, and anti-tumor activities, treat oral and digestive tract inflammation or (and) ulcer-related diseases, and have bi-directional immunomodulatory effects.

SUMMARY OF THE INVENTION

The first technical problem solved with the invention is providing new uses of *Paliurus ramosissimus* (Lour.) Poir.

When applying *Paliurus ramosissimus* (Lour.) Poir., the whole plant or any part is used; wherein, the medicinal part can be any part or the mix of roots, stems, leaves, flowers, and fruits.

Specifically, the new medicinal uses of *Paliurus ramosissimus* (Lour.) Poir. are its uses in preparation of drugs with anti-fibrotic, anti-fungal, and anti-tumor activities, for the treatment of oral and digestive tract inflammation or (and) ulcer-related diseases, or with bi-directional immunomodulatory effects.

The second technical problem solved with the invention is providing a new *Paliurus ramosissimus* (Lour.) Poir. extract. Given the ease of collection of and convenience of storage of medicinal materials, in order to facilitate clinical application, *Paliurus ramosissimus* (Lour.) Poir. can be applied after being prepared as extract.

Specifically, the *Paliurus ramosissimus* (Lour.) Poir. extract in the present invention is prepared from the whole plant or any part of *Paliurus ramosissimus* (Lour.) Poir. as pharmaceutical raw materials, with conventional extraction methods. The main ingredients of *Paliurus ramosissimus* (Lour.) Poir. extract obtained in the present invention include flavonoids, triterpenoids, alkaloids, coumarins; further include glycosides and monomer ingredients of the above-described flavonoids, triterpenoids, alkaloids, and coumarins; additionally include polysaccharides and celluloses.

The third technical problem solved with the invention is providing methods for preparing aliurus *ramosissimus* (Lour.) Poir. extract as follows:

Method I:

A, with the whole or any part of *Paliurus ramosissimus* as raw material for extraction; and, B, extracting the raw materials with solvent, and drying the extracted material;

In the above technical scheme, *Paliurus ramosissimus* (Lour.) Poir. as pharmaceutical raw materials mentioned in Step A is its fresh products, freeze-dried products, and organic solvent pretreatment products.

In the above technical scheme, the solvent mentioned in Step B is methanol, ethanol, isopropanol, ethyl acetate or petroleum ether; preferably, methanol or ethanol.

In the above technical scheme, the extraction mentioned in Step B is soak, reflux or percolation extraction.

In the above technical scheme, the drying mentioned in Step B is reduced pressure drying, freeze drying, spray drying or microwave drying.

Method II:

A, with the whole or any part of *Paliurus ramosissimus* as raw material for extraction;

B, extracting the raw materials with solvent "a", and concentrating the extracted solution to get the concentrate, and;

C, extracting the concentrate obtained in step B with solvent "b" and drying;

Or, drying the concentrate obtained in Step B before extracting it with solvent b, and drying.

In the above technical scheme, *Paliurus ramosissimus* (Lour.) Poir. as pharmaceutical raw materials mentioned in Step A is its fresh or freeze-dried form or pretreated form with organic solvent.

In the above technical scheme, the solvent a mentioned in Step B is methanol, ethanol, isopropanol; preferably, methanol or ethanol.

In the above technical scheme, the solvent b mentioned in Step C is ethyl acetate or petroleum ether.

In the above technical scheme, the extraction mentioned in Step B and Step C is soak method, reflux method, percolation method or extraction method.

In the above technical scheme, the drying mentioned in Step B and Step C is reduced pressure drying, freeze drying, spray drying or microwave drying.

For the extract prepared with the above-described methods, if it is prepared with Method I, it is named as the extract corresponding to the solvent used in Step B, such as *Paliurus ramosissimus* (Lour.) Poir. ethanol extract, *Paliurus ramosissimus* (Lour.) Poir. methanol extract, *Paliurus ramosissimus* (Lour.) Poir. isopropanol extract, *Paliurus ramosissimus* (Lour.) Poir. ethyl acetate extract, and *Paliurus ramosissimus* (Lour.) Poir. petroleum ether extract; if it is prepared with Method II, it is named as the extract corresponding to the solvent b used in Step C, such as *Paliurus ramosissimus* (Lour.) Poir. petroleum ether extract and *Paliurus ramosissimus* (Lour.) Poir. ethyl acetate extract, while extract 1 obtained in Step C of Method II is named as the extract corresponding to the solvent a used in the Step B of Method II, such as *Paliurus ramosissimus* (Lour.) Poir. ethanol extract, *Paliurus ramosissimus* (Lour.) Poir. methanol extract, and *Paliurus ramosissimus* (Lour.) Poir. isopropanol extract.

In the above technical scheme, the amount relationship between the solvent used in Step B of Method I is that, the amount of the solvent is 1-20 times of that of the weight of *Paliurus ramosissimus* (Lour.) Poir.; preferably, the amount of the solvent is 5-15 times of that of the weight of *Paliurus ramosissimus* (Lour.) Poir.; further, the amount of the solvent is 8-10 times of that of the weight of *Paliurus ramosissimus* (Lour.) Poir.

In the above technical scheme, the amount relationship between the solvent a used in Step B of Method II is that, the amount of the solvent a is 1-20 times of that of the weight of *Paliurus ramosissimus* (Lour.) Poir.; preferably, the amount of the solvent a is 5-15 times of that of the weight of *Paliurus ramosissimus* (Lour.) Poir.; further, the amount of the solvent a is 8-10 times of that of the weight of *Paliurus ramosissimus* (Lour.) Poir.

Preferably, when the solvent or solvent a is methanol or ethanol, the amount of methanol or ethanol is 1-20 times of that of the weight of *Paliurus ramosissimus* (Lour.) Poir.; Preferably, the amount of methanol or ethanol is 5-15 times of that of the weight of *Paliurus ramosissimus* (Lour.) Poir.; Further, the amount of methanol or ethanol is preferably 8-10 times of that of the weight of *Paliurus ramosissimus* (Lour.) Poir.

Wherein, the concentration of the mentioned ethanol is 10-95%. Preferably, the concentration of ethanol is 50-95%. Most preferably, the concentration of ethanol is 95%.

In the above technical scheme, the raw material *Paliurus ramosissimus* (Lour.) Poir. before treatment with organic solvents must be fresh products or freeze-dried product. The reason is that, the inventors have found that sun and air dried product or oven dried product do not have the corresponding activities, so fresh *Paliurus ramosissimus* (Lour.) Poir. product is used as raw materials. However, the fresh product is not good for storage and transportation, so the inventors have identified that freeze-dried and organic solvent pretreated *Paliurus ramosissimus* (Lour.) Poir. retains active ingredients, which has equivalent effects to the fresh product, meets the new uses of *Paliurus ramosissimus* (Lour.) Poir. extract in the present invention, and is good for storage and transportation.

Specifically, the organic solvent treatment method is as follows: take *Paliurus ramosissimus* (Lour.) Poir., soak in an organic solvent, and dry.

Wherein, the mentioned organic solvent is ethanol, methanol, ethyl acetate, petroleum ether, isopropanol and the like; preferably methanol or ethanol.

The extract in the present invention may be administered via oral (including buccal or sublingual), nasal, topical (including buccal, sublingual or transdermal), or parenteral (including subcutaneous, intradermal, intramuscular, intraarticular, intrasynovial, intrasternal, intrathecal, intralesional, intravenous, or intradermal injection or infusion) route. These preparations can be prepared with any method known in pharmaceutical technology, for example, being prepared by combining the active ingredient with the carrier or excipient.

The fourth technical problem solved with the invention is providing pharmaceutical preparations prepared from the extract of *Paliurus ramosissimus* (Lour.) Poir. in the present invention, i.e., a variety of preparations of different routes of administration by adding pharmaceutically acceptable excipient to the extract of *Paliurus ramosissimus* (Lour.) Poir. in the present invention. For the ease of application, the extract in the present invention can be prepared to conventional oral preparations, injection preparations and topical preparations by conventional methods. These preparations can be prepared with any method known in pharmaceutical technology, for example, being prepared by combining the active ingredient with the carrier or excipient. For example, preparations administered via oral (including buccal or sublingual), nasal, topical (including buccal, sublingual or transdermal), or parenteral (including subcutaneous, intradermal, intramuscular, intraarticular, intrasynovial, intrasternal, intrathecal, intralesional, intravenous, or intradermal injection or infusion) route. Such as tablets, capsules, granules, pellets, microspheres, pills, controlled release preparations, sustained release preparations or injections.

Pharmaceutical preparations which are suitable for oral administration may be presented as individual units such as capsules, tablets, powders or granules; aqueous or non-aqueous liquid solutions, suspensions, oil-in-water liquid emulsions or water-in-oil emulsions. It can be prepared as oral liquids in unit dosage form, such as solutions, syrups and elixirs. Syrups can be prepared by dissolving the compound in appropriately flavored aqueous solutions, and elixirs are prepared by non-toxic vehicles. Solubilizing agents and emulsifiers (such as ethoxylated isostearyl alcohol and polyoxyethylene sorbitol ether), preservatives, flavoring additives (such as peppermint oil or natural sweeteners, or saccharin or other artificial sweeteners), etc. can also be added. Where appropriate, preparations in dosage form which are suitable for oral administration may be microencapsulated, and may also be prepared by coating or embedding particulate material in polymers, wax or the like for prolonged or sustained release. It can also be administered in the form of liposome delivery system (such as small unilamellar vesicles, large unilamellar vesicles and multilamellar liposomes); liposomes may be formed by a variety of phospholipids, such as cholesterol, stearylamine or phosphatidylcholines.

Pharmaceutical preparations which are suitable for transdermal administration may be in the form of individual patches intended to remain close contact with the epidermis of the recipient for a longer period. Pharmaceutical preparations which are suitable for topical administration may be formulated as ointments, creams, suspensions, lotions, powders, solutions, pastes, gels, spray, aerosol, liniment or oil.

The fifth technical problem solved with the invention is providing the new medicinal uses of *Paliurus ramosissimus* (Lour.) Poir. in the present invention.

The *Paliurus ramosissimus* (Lour.) Poir. extract, including *Paliurus ramosissimus* (Lour.) Poir. methanol extract, *Paliurus ramosissimus* (Lour.) Poir. ethanol extract, *Paliurus ramosissimus* (Lour.) Poir. ethyl acetate extract, *Paliurus ramosissimus* (Lour.) Poir. petroleum ether extract, all have good anti-fibrotic, anti-fungal, and anti-tumor activities, treat oral and digestive tract inflammation or (and) ulcer-related diseases, and have bi-directional immunomodulatory effects. It includes the above new pharmaceutical uses of *Paliurus ramosissimus* (Lour.) Poir. extract alone or drug combination with main active ingredient of *Paliurus ramosissimus* (Lour.) Poir. extract.

Wherein:

When applying the *Paliurus ramosissimus* (Lour.) Poir. extract in the present invention to prepare anti-tumor drugs, combination of other Chinese traditional medicines and western medicines with tumor therapeutic effects can be added, including radiotherapy, immunotherapy, chemotherapeutic agents that damage DNA, chemotherapeutic agents that interfere with cell replication, immunomodulatory drugs, specifically topoisomerase I inhibitors, topoisomerase II inhibitors, alkylating agents, DNA chimeric agents, DNA intercalating agents and radical generating agents, chemotherapeutic agents that interfere with cell replication, protein tyrosine kinase inhibitors, protease inhibitors, antibodies, proteins or enzyme inhibitors that bind to over-expressed proteins in tumor and down regulate cell replication. Other Chinese traditional medicines and western medicines may be selected from: irinotecan, topotecan, camptothecin and analogs or metabolites, doxorubicin, etoposide, teniposide, daunorubicin, melphalan, chlorambucil, busulfan, tespamin, ifosfamide, carmustine, lomustine, semustine, streptozotocin, decarbazine, methotrexate, mitomycin C, cyclophosphamide, cisplatin, oxaliplatin, carboplatin, bleomycin, 5-fluorouracil, capecitabine, gemcitabine, fludarabine, cytarabine, mercaptopurine, thioguanine, pentostatin, hydroxyurea, paclitaxel, docetaxel and related analogs, vincristine, vinblastine and related analogs, thalidomide and related analogs, imatinib mesylate, gefitinib, bortezomib, trastuzumab, rituximab, cetuximab, bevacizumab, cinobufotalin, *Agaricus* blazei, tree falsespiraea bark ethyl acetate extract, Litchi water extract, tripterine, grifola polysaccharide, carboxymethyl tuckahoe polysaccharide, alisol extract concentrates, licorice polysaccharide, *angelica* total polysaccharides, psoralen, and *chinensis* polysaccharide.

When applying the *Paliurus ramosissimus* (Lour.) Poir. extract in the present invention to prepare anti-fibrotic drugs, combination of other Chinese traditional medicines and western medicines with fibrosis therapeutic effects can be added. Other Chinese medicines and western medicines with fibrosis therapeutic effects are selected from: *panax notoginseng* saponins, ligustrazine, *Salvia* miltiorrhiza, *Acanthopanax* injection, ligustrazine injection, safflower injection, Ginkgo flavonol glycosides, Shengmai, *Salvia* miltiorrhiza injection, Shuanghuanglian, Xiangdan injection, Yiqihuoxue granules, Kangxian granules, Feikang granules, *lilium* compound antiphlogistic pills, powder *cordyceps* gecko *ginseng* pills, *astragalus*, saffron, Radix Rehmanniae, *panax notoginseng*, *Gynostemma pentaphylla*, *Curcuma longa*, abelmosk, amygdalin, tetrandrine, emodin, entecavir, lamivudine, β-carotene, vitamin E, phosphatidylcholine, S-adenosylmethionine, alprostadil, dinoprostone, colchicine alkali, estrogen, angiotensin II receptor blockers, sympathetic nervous system inhibitors, interferons, prolyl-4-hydroxylase inhibitors, heparin, silymarin, and ursodeoxycholic acid. The said fibrosis includes pulmonary fibrosis, renal fibrosis, liver fibrosis, and myocardial fibrosis.

When applying the *Paliurus ramosissimus* (Lour.) Poir. extract in the present invention to prepare drugs with bi-directional immunomodulatory effects, specifically referring to applying to prepare drugs for compromised immune function or (and) autoimmune diseases, especially compromised immune function or (and) autoimmune diseases caused by immune dysfunction. Wherein the said compromised immune function caused by immune dysfunction includes susceptibility to colds, weakness, cancer, and AIDS, and said autoimmune diseases caused by immune dysfunction includes rheumatoid arthritis, lupus, scleroderma, hyperthyroidism, juvenile diabetes, idiopathic thrombocytopenic purpura, autoimmune hemolytic anemia, ulcerative colitis, and chronic liver disease.

In the Above Technical Scheme, when Applying the *Paliurus ramosissimus* (Lour.) Poir. Extract to Prepare Anti-Tumor Drugs, the Whole Plant or any Part of *Paliurus Ramosissimus* (Lour.) Poir. Can be Used as Pharmaceutical Raw Material, Preferably Leaf as Pharmaceutical Raw Material.

When using the whole plant including whole root, stem and leaf, or any part of *Paliurus ramosissimus* (Lour.) Poir. as pharmaceutical raw material, *Paliurus ramosissimus* (Lour.) Poir. extract may be prepared using the following method: take the fresh or freeze-dried product of the whole plant including whole root, stem and leaf, or any part of *Paliurus ramosissimus* (Lour.) Poir., pre-treat *Paliurus ramosissimus* (Lour.) Poir. fresh or freeze-dried product with an organic solvent for future use; when preparing, extract the above pre-treated *Paliurus ramosissimus* (Lour.) Poir. fresh or freeze-dried product with an organic solvent. Or directly extract *Paliurus ramosissimus* (Lour.) Poir. fresh or freeze-dried product with an organic solvent to obtain *Paliurus ramosissimus* (Lour.) Poir. extract. Organic solvent extraction methods include, but are not limited to, conventional extraction methods in the field such as soak method, reflux method, and percolation method.

The said *Paliurus ramosissimus* (Lour.) Poir. prior to organic solvent treatment is preferably fresh or freeze-dried product.

The said organic solvent is selected from methanol, ethanol, isopropanol, ethyl acetate and petroleum ether, preferably 50-95% ethanol, more preferably 95% ethanol.

*Paliurus ramosissimus* (Lour.) Poir. extract is preferably prepared using the following method: take the whole plant of fresh *Paliurus ramosissimus* (Lour.) Poir., add 95% ethanol of 8-10 times the weight, soak for one day, then crush the *Paliurus ramosissimus* (Lour.) Poir., add 95% ethanol of 6-10 times the weight, soak for 2-3 days, collect the extract liquid, recover the solvent under reduced pressure to obtain concentrated extract liquid, and dry to obtain *Paliurus ramosissimus* (Lour.) Poir. ethanol extract. Wherein, the drying methods include, but are not limited to, reduced pressure drying, freeze drying, spray drying, and microwave drying.

More preferably, take stems and leaves of fresh *Paliurus ramosissimus* (Lour.) Poir., add 95% ethanol of 8 times the weight, soak for one day, then crush the *Paliurus ramosissimus* (Lour.) Poir., add 95% ethanol of 10 times the weight, reflux to extract, collect the extract liquid, recover ethanol at 60° C. under reduced pressure until no ethanol smell to obtain concentrated extract liquid, and dry to obtain *Paliurus ramosissimus* (Lour.) Poir. ethanol extract.

More preferably, take stems and leaves of fresh *Paliurus ramosissimus* (Lour.) Poir., add methanol of 8 times the weight, soak for one day, then crush the *Paliurus ramosissimus* (Lour.) Poir., add methanol of 10 times the weight, reflux to extract, collect the extract liquid, recover methanol at 60° C. under reduced pressure to obtain concentrated extract liquid, and dry to obtain *Paliurus ramosissimus* (Lour.) Poir. methanol extract.

Further, disperse *Paliurus ramosissimus* (Lour.) Poir. ethanol extract in water, extract with petroleum ether and ethyl acetate in sequence, and concentrate and dry to obtain petroleum ether extract or ethyl acetate extract.

Further, specific steps of the said alcohol extraction are as follows:

(1) Take the leaves of *Paliurus ramosissimus* (Lour.) Poir., add 50%-95% ethanol of 5-15 times the weight, and soak;

(2) crush the leaves, add 50%-95% ethanol of 5-15 times the weight to extract ingredients soluble in alcohol;

(3) collect the extract liquid, recover ethanol at 30-70° C. under reduced pressure until no alcohol smell to obtain the extract;

(4) freeze-dry the concentrated extract liquid to obtain *Paliurus ramosissimus* (Lour.) Poir. leaf alcohol extract.

Further, extract the said Chinese traditional medicine extract with petroleum ether or ethyl acetate. Extract the said Chinese traditional medicine extract with petroleum ether, ethyl acetate and n-butanol in sequence, recover solvents and freeze dry to obtain extracts at three polar parts, dissolve in isopropanol, and test its inhibitory effect on tumor cells. The results are that the Chinese traditional medicine extracts at petroleum ether part and ethyl acetate part have good anti-tumor activity while extract at n-butanol part has no anti-tumor activity, and extract at ethyl acetate part has better anti-tumor activity.

Further, the main ingredients of *Paliurus ramosissimus* (Lour.) Poir. extract include triterpenoids, flavonoids, alkaloids and coumarins.

In the Above Technical Scheme, when Applying the *Paliurus ramosissimus* (Lour.) Poir. Extract in the Present Invention to Prepare Anti-Fibrotic Drugs, the Whole Plant or any Part of *Paliurus ramosissimus* (Lour.) Poir. Can be Used as Pharmaceutical Raw Material, Preferably Leaf as Pharmaceutical Raw Material.

When using the whole plant including whole root, stem and leaf, or any part of *Paliurus ramosissimus* (Lour.) Poir. as pharmaceutical raw material, *Paliurus ramosissimus* (Lour.) Poir. extract may be prepared using the following method: take the fresh or freeze-dried product of the whole plant including whole root, stem and leaf, or any part of *Paliurus ramosissimus* (Lour.) Poir., pre-treat *Paliurus ramosissimus* (Lour.) Poir. fresh or freeze-dried product with an organic solvent for future use; when preparing, extract the above pre-treated *Paliurus ramosissimus* (Lour.) Poir. fresh or freeze-dried product with an organic solvent. Or directly extract *Paliurus ramosissimus* (Lour.) Poir. fresh or freeze-dried product with an organic solvent to obtain *Paliurus ramosissimus* (Lour.) Poir. extract. Organic solvent extraction methods include, but are not limited to, conventional extraction methods in the field such as soak method, reflux method, and percolation method.

The said *Paliurus ramosissimus* (Lour.) Poir. prior to organic solvent treatment is preferably fresh or freeze-dried product.

The said organic solvent is selected from methanol and 10-100% ethanol, preferably 95% ethanol.

*Paliurus ramosissimus* (Lour.) Poir. extract is preferably prepared using the following method: take the whole plant of fresh *Paliurus ramosissimus* (Lour.) Poir., add 95% ethanol of 8-10 times the weight, soak for one day, then crush the *Paliurus ramosissimus* (Lour.) Poir., add 95% ethanol of 6-10 times the weight, soak for 2-3 days, collect the extract liquid, recover the solvent under reduced pressure to obtain concentrated extract liquid, and dry to obtain *Paliurus ramosissimus* (Lour.) Poir. ethanol extract. Wherein, the drying methods include, but are not limited to, reduced pressure drying, freeze drying, spray drying, and microwave drying.

More preferably, take stems and leaves of fresh *Paliurus ramosissimus* (Lour.) Poir., add 95% ethanol of 8 times the weight, soak for one day, then crush the *Paliurus ramosissimus* (Lour.) Poir., add 95% ethanol of 10 times the weight, reflux to extract, collect the extract liquid, recover ethanol at 60° C. under reduced pressure until no ethanol smell to obtain concentrated extract liquid, and dry to obtain *Paliurus ramosissimus* (Lour.) Poir. ethanol extract.

More preferably, take stems and leaves of fresh *Paliurus ramosissimus* (Lour.) Poir., add methanol of 8 times the weight, soak for one day, then crush the *Paliurus ramosissimus* (Lour.) Poir., add methanol of 10 times the weight, reflux to extract, collect the extract liquid, recover methanol at 60° C. under reduced pressure to obtain concentrated extract liquid, and dry to obtain *Paliurus ramosissimus* (Lour.) Poir. methanol extract.

Further, disperse *Paliurus ramosissimus* (Lour.) Poir. ethanol extract in water, extract with petroleum ether and ethyl acetate in sequence, and concentrate and dry to obtain petroleum ether extract or ethyl acetate extract.

In the Above Technical Scheme, when Applying the *Paliurus ramosissimus* (Lour.) Poir. Extract to Prepare Antifungal Drugs, the Whole Plant or any Part of *Paliurus Ramosissimus* (Lour.) Poir. Can be Used as Pharmaceutical Raw Material, Preferably Leaf as Pharmaceutical Raw Material.

*Paliurus ramosissimus* (Lour.) Poir. extract is prepared using the following method: take the whole plant or any part of *Paliurus ramosissimus* (Lour.) Poir., add methanol or ethanol of 1-20 times of its volume, or further extract methanol or ethanol extract with ethyl acetate or petroleum ether; concentrate extract liquid, and dry to obtain *Paliurus ramosissimus* (Lour.) Poir. extract.

The said *Paliurus ramosissimus* (Lour.) Poir. is preferably fresh product, freeze-dried product, or methanol or product treated with ethanol; the said extraction methods include soak, reflux, and percolation; the said drying methods include reduced pressure drying, freeze drying, spray drying, and microwave drying.

The said *Paliurus ramosissimus* (Lour.) Poir. extract includes triterpenoids, flavonoids, alkaloids, coumarins, and glycosides and monomer of the triterpenoids, flavonoids, alkaloids, coumarins.

The said various preparations of *Paliurus ramosissimus* (Lour.) Poir. extract include *Paliurus ramosissimus* (Lour.) Poir. extract tablets, granules, ointments, gels, plastics, liniment, lotions and spray.

The invention is providing *Paliurus ramosissimus* (Lour.) Poir. extract and preparations with antifungal activity in the application of antifungal activity. The said *Paliurus ramosissimus* (Lour.) Poir. extract includes *Paliurus ramosissimus* (Lour.) Poir. methanol, ethanol, ethyl acetate, petroleum ether or similar solvents extract. *Paliurus ramosissimus* (Lour.) Poir. fresh product, freeze-dried product, methanol (ethanol) or other organic solvent pre-treated product is used as raw material to ensure the stability of active ingredients.

In the Above Technical Scheme, when Applying the *Paliurus ramosissimus* (Lour.) Poir. Extract to Prepare Drugs for Compromised Immune Function or (and) Autoimmune Diseases, the Whole Plant or any Part of *Paliurus ramosissimus* (Lour.) Poir. Can be Used as Pharmaceutical Raw Material, Preferably Leaf as Pharmaceutical Raw Material.

*Paliurus ramosissimus* (Lour.) Poir. extract is prepared using the following method: take the whole plant or any part of *Paliurus ramosissimus* (Lour.) Poir., add methanol or ethanol of 1-20 times of its volume, or further extract methanol or ethanol extract with ethyl acetate or petroleum ether; concentrate extract liquid, and dry to obtain *Paliurus ramosissimus* (Lour.) Poir. extract.

The said *Paliurus ramosissimus* (Lour.) Poir. extract, *Paliurus ramosissimus* (Lour.) Poir. is preferably fresh product, freeze-dried product, or methanol, ethanol or isopropanol pre-treated product; the extraction methods include soak, reflux, and percolation; the drying methods include reduced pressure drying, freeze drying, spray drying, and microwave drying.

The said *Paliurus ramosissimus* (Lour.) Poir. extract, ingredients include triterpenoids, flavonoids, alkaloids, coumarins, polysaccharides, celluloses and glycosides and monomers of triterpenoids, flavonoids, alkaloids and coumarins.

The said *Paliurus ramosissimus* (Lour.) Poir. extract preparations include *Paliurus ramosissimus* (Lour.) Poir. extract tablets, capsules, pastes, granules, injections, suppositories, ointments, gels, plastics, liniments, lotions and sprays.

The said *Paliurus ramosissimus* (Lour.) Poir. extract, it is used in preparation of drugs for compromised immune function related diseases or (and) autoimmune diseases, including using *Paliurus ramosissimus* (Lour.) Poir. extract alone or medicine compounds with *Paliurus ramosissimus* (Lour.) Poir. extract as the main active ingredient in the application of preparing drugs for compromised immune function related diseases or (and) autoimmune diseases.

In the Above Technical Scheme, when Applying *Paliurus ramosissimus* (Lour.) Poir. Extract to Prepare Drugs for the Treatment of Oral and Digestive Tract Inflammation or (and) Ulcer, the Whole Plant or any Part of *Paliurus ramosissimus* (Lour.) Poir. Can be Used as Pharmaceutical Raw Material, Preferably Leaf as Pharmaceutical Raw Material.

*Paliurus ramosissimus* (Lour.) Poir. extract is prepared using the following method: take fresh product of *Paliurus ramosissimus* (Lour.) Poir. leaves, *Paliurus ramosissimus* (Lour.) Poir. stems and leaves, or *Paliurus ramosissimus* (Lour.) Poir. whole plant, add methanol or ethanol of 1-20 times of its volume to extract; or further extract methanol or ethanol extract with ethyl acetate or petroleum ether; concentrate extract liquid, and dry to obtain *Paliurus ramosissimus* (Lour.) Poir. extract; ingredients include triterpenoids, flavonoids, alkaloids, coumarins, polysaccharides, celluloses and glycosides and monomers of triterpenoids, flavonoids, alkaloids and coumarins.

The said *Paliurus ramosissimus* (Lour.) Poir. extract, extract *Paliurus ramosissimus* (Lour.) Poir. fresh product or freeze-dried product directly with organic solvents, or extract after pre-treating *Paliurus ramosissimus* (Lour.) Poir. fresh product with organic solvents; organic solvents include methanol, ethanol, isopropanol, ethyl acetate, petroleum ether; the said extraction methods include soak, reflux or percolation; the said drying methods include reduced pressure drying, freeze drying, spray drying or microwave drying.

The said *Paliurus ramosissimus* (Lour.) Poir. extract preparations include tablets, capsules, pastes, granules, injections, suppositories, ointments, gels, plastics, liniments, lotions and sprays.

The application of *Paliurus ramosissimus* (Lour.) Poir. extract includes using *Paliurus ramosissimus* (Lour.) Poir. extract alone or medicine compounds with *Paliurus ramosissimus* (Lour.) Poir. extract as the main active ingredient in the application of preparing drugs for treatment of oral and digestive tract inflammation or (and) ulcer.

DETAILED DESCRIPTION

The following detailed description, in the form of embodiment, further describes the aforementioned content in the present invention in details, and it illustrates but does not limit the invention.

The study on ingredients of *Paliurus ramosissimus* (Lour.) Poir. extract is as follows.

Preparation of sample test solution: take 1 g of the extract sample, dissolve in 25 ml of anhydrous ethanol, and centrifuge. Take 2 ml of the supernatant, dilute 5-fold with ethanol to a final concentration of 0.008 g/ml.

(1) Identification of Triterpenoids

A. L-B Reaction

Dissolve the sample in acetic anhydride, add a few drops of concentrated sulfuric acid-acetic anhydride (1:20), yellow→red→purple→blue color changes appear, and the color finally fades, indicating the presence of triterpenoids.

B. Kahlenberg Reaction

Spot the sample in chloroform or alcohol solution on filter paper, spray 20% antimony pentachloride in chloroform solution (or saturated antimony trichloride in chloroform solution), heat at 60-70° C. after drying, blue appears, indicating the presence of triterpenoids.

C. R—H Reaction

Spot sample test solution on filter paper, spray 25% trichloroacetic acid in ethanol solution, heat to 100° C., red appears and gradually becomes purple, indicating the presence of triterpenoids.

D. Salkowki Reaction

Dissolve the sample in chloroform, add concentrated sulfuric acid, the sulfuric acid layer appears red or blue, and the chloroform layer appears green fluorescence, indicating triterpenoids.

E. Tschugaeff Reaction

Dissolve the sample in glacial acetic acid, add a few drops of acetyl chloride and a few grains of zinc chloride crystal, mildly heat, it appears pale pink or purple, indicating the presence of triterpenoids.

(2) Identification of Flavonoids

A. Hydrochloric Acid—Magnesium Reduction Reaction (Chromogenic Reduction Reaction)

Dissolve a small amount of sample in 1 ml of ethanol, and add a little magnesium powder and concentrated hydrochloric acid, shake for a while, and purple appears, indicating the presence of flavonoids.

B. Aluminum Trichloride Reaction (Chromogenic Metal Ions Complexation)

Apply the sample test solution on filter paper with a glass rod, blow to dryness, spray 1% aluminum chloride in ethanol solution, blow to dryness, place under a UV lamp and bright yellow appears, indicating the presence of flavonoids.

C. Ferric Chloride Reaction (Chromogenic Metal Ions Complexation)

Apply the sample test solution on filter paper with a glass rod, blow to dryness, observe the fluorescence under ultraviolet light, spray 3% ferric chloride in ethanol solution, blow to dryness, a dark blue fluorescent spot appears and turns into a brown fluorescent spot after being smoked by ammonia, indicating the presence of flavonoids.

D. Chromogenic Reaction with Alkaline Reagent

Apply the sample test solution on filter paper with a glass rod, dry, spray sodium hydroxide solution or exposure to ammonia vapors, observe under sunlight light, and ammonia vapor turns sample spot to bright yellow, indicating the presence of flavonoids.

(3) Identification of Alkaloids

A. Modified Bismuth Potassium Iodide (Dragendorff) Method

① Dissolve 0.85 g of bismuth nitrate in 10 ml of glacial acetic acid and 40 ml of water; ② Dissolve 8 g of potassium iodide in 20 ml of water. Mix the equal amount of ① ② test solutions, place in a brown bottle as the stock solution. Before use, mix 1 ml of the stock solution, 4 ml of glacial acetic acid and 12 ml of water. Add the sample test solution into the above reagent, the solution becomes reddish brown, and after adding distilled water and shaking, precipitate forms, indicating the presence of alkaloids.

B. Iodine—Potassium Iodide (Wagner) Method

Dissolve 1 g of iodine and 10 g of potassium iodide in 50 ml of water, add 2 ml of acetic acid, and add water to 100 ml. Take appropriate amount of the above reagent, add 1 ml of the sample test solution, and the solution becomes brown, indicating the presence of alkaloids.

C. Silicotungstic Acid (Bertrand) Method

Dissolve 5 g of silicotungstic acid in 100 ml of water, add a small amount of concentrated hydrochloric acid to adjust pH to approximately 2. Take appropriate amount of the above reagent, add 1 ml of the sample test solution, and the solution becomes brown, indicating the presence of alkaloids.

(4) Identification of coumarins

A. Iron-hydroxamate reaction

① a. Dissolve 20 g of hydroxylamine hydrochloride in 50 ml of water, dilute to 200 ml with ethanol, store in a cool place; b. dissolve 50 g of potassium hydroxide in a little water, add 500 ml of ethanol. ② Dissolve 10 g of ferric chloride (FeCl$_3$. 6H$_2$O) in 20 ml 36% hydrochloric acid solution, add 200 ml of ethyl ether, shake well, and store in a sealed container. When using, mix one portion of ① a. and 2 portions of ① b, filter the precipitate, and store the filtrate in a fridge. Apply the sample test solution on filter paper with a glass rod, spray a. b. mixture test solution, slightly dry, then spray test solution ②, and red color appears, indicating the presence of coumarins.

B. Diazotization Reaction

① Dissolve 0.35 g of paranitroaniline in 5 ml of concentrated hydrochloric acid, add water to 50 ml; ② add 50 ml of water to 5 g of sodium nitrite. Take the same amount of ①, ② solutions, and mix in an ice-water bath for future use. Take a small amount of the sample, add diazonium reagent dropwise, and orange-red appears, indicating the presence of coumarins.

These studies have identified that the main ingredients of *Paliurus ramosissimus* (Lour.) Poir. extract in the present invention include flavonoids, triterpenoids, alkaloids, coumarins, and glycosides and monomers of the above flavonoids, triterpenoids, alkaloids, coumarins, as well as polysaccharides and celluloses.

I. The Antitumor Activity of *Paliurus ramosissimus* (Lour.) Poir. Leaf Extract

1. Extraction from *Paliurus ramosissimus* (Lour.) Poir. Leaves (1) Take 1 kg of *Paliurus ramosissimus* (Lour.) Poir. fresh leaves, add 8-10 times of 95% ethanol for 1-2 days (purpose: 1. to deactivate the activity of enzymes in fresh leaves, thus avoiding the destruction of active ingredients; 2. to increase fresh leaves hardness, thus facilitating the next crushing process), crush fresh leaves, then add 10 times of 95% ethanol (60-100% ethanol extraction), soak for three days to extract alcohol-soluble ingredients. Collect the extract liquid, recover ethanol at 30-40° C. under reduced pressure to no alcohol smell, and further freeze-dry the extract concentrated liquid to obtain *Paliurus ramosissimus* (Lour.) Poir. fresh leaf ethanol extract.

(2) Dry the extraction residue, add 8 to 10 times of water, soak for three days to extract water-soluble ingredients, collect the extract liquid, and freeze-dry to obtain *Paliurus ramosissimus* (Lour.) Poir. fresh leaf aqueous extract.

(3) Extract *Paliurus ramosissimus* (Lour.) Poir. dry products (natural drying at room temperature) as the method described above to obtain *Paliurus ramosissimus* (Lour.) Poir. dry product alcohol extract and water extract.

(4) Soak *Paliurus ramosissimus* (Lour.) Poir. fresh leaves in ethanol, dry in a dark place to obtain dry leaves, and extract the obtained dry leaves after soaking in ethanol and dryness as the method described above to obtain alcohol extract and water extract.

2. Anti-Tumor Activity

The study compares antitumor activity of *Paliurus ramosissimus* (Lour.) Poir. leaf extract. Take a variety of tumor cells in logarithmic growth phase (tumor cell lines used are the followings: cervical carcinoma cell line Hela; human hepatoma cell line SMMC-7721; human lung carcinoma cell line A549; human colon carcinoma cell line Caco-2; leukemia cell line K562; gastric carcinoma cell line MGC-803;), centrifuge at 2000 rpm for 5 min, adjust precipitate cell concentration of cell suspension to $1 \times 10^5$ cells/ml with corresponding culture medium containing 10% fetal bovine serum, and seed cells in 96-well culture plates. To each well, add 200 μl of cell suspension, respectively add sterile extract solution of certain concentration to make the final concentration of extract in each well is 0.02, 0.1, 0.2, 0.4, 0.5, 0.8, 1.0, 2.0 mg/ml, mix well, place in 37° C., 5% CO$_2$ incubator for 24 h, precipitate the culture, wash twice with PBS, to each well, add 20 μl of 5 mg/ml MTT phosphate buffer and 150 μl of culture medium, culture under the same conditions for 4 h, and then terminate the culture. Centrifuge at 2000 rpm for 5 min, then discard the culture medium in wells, to each well, add 150 μl of DMSO, shake for 10 min so that the formed formazan particles are fully dissolved, and determine absorbance with microplate reader. Select 570 nm as the measurement wavelength. Calculate IC50 of the extract to tumor cells. The results are shown in Table 1.

TABLE 1

Inhibition effects of *Paliurus ramosissimus* (Lour.) Poir. extract on different tumor cells:

| Cell line | Hela | SMMC-7721 | A549 | Caco-2 | MGC-803 |
|---|---|---|---|---|---|
| *Paliurus ramosissimus* (Lour.) Poir. Fresh leaf alcohol extract | 0.0473 mg/ml | 0.1957 mg/ml | 0.0126 mg/ml | 0.1174 mg/ml | 0.2367 mg/ml |
| *Paliurus ramosissimus* (Lour.) Poir. Fresh leaf water extract | — | — | — | — | — |
| *Paliurus ramosissimus* (Lour.) Poir. Dried leaf alcohol extract | — | — | — | — | — |
| *Paliurus ramosissimus* (Lour.) Poir. Dried leaf water extract | — | — | — | — | — |

TABLE 1-continued

Inhibition effects of Paliurus ramosissimus (Lour.) Poir. extract on different tumor cells:

| Cell line | Hela | SMMC-7721 | A549 | Caco-2 | MGC-803 |
|---|---|---|---|---|---|
| Alcohol extract of Paliurus ramosissimus (Lour.) Poir. Leaf soaked in ethanol and air dried | 0.0442 mg/ml | 0.2038 mg/ml | 0.0175 mg/ml | 0.1060 mg/ml | 0.2512 mg/ml |
| Water extract of Paliurus ramosissimus (Lour.) Poir. Leaf soaked in ethanol and air dried | — | — | — | — | — |

The results have showed that, Paliurus ramosissimus (Lour.) Poir. fresh leaf alcohol extract and alcohol extract of Paliurus ramosissimus (Lour.) Poir. leaf soaked in ethanol and air dried have good anti-tumor activity, while other extracts do not have anti-tumor activity. The reasons may be related to the solubility and stability of the active extract.

3. Determination of Ingredient Content in Paliurus ramosissimus (Lour.) Poir. Leaf Alcohol Extract (1) Determination of Triterpenoids Content Take three portions of approximately 0.1 g of the coarse powder of this product, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of alcohol extract contains 0.052±0.010 g of triterpenoids.

(2) Determination of Flavonoids Content

Take three portions of approximately 0.1 g (equivalent to 2 g raw material) of the coarse powder of this product, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance, and calculate total flavonoids content in sample test solution (flavonoids as rutin). The calculation has showed that 1 g of alcohol extract contains 0.325±0.043 g of flavonoids.

(3) Determination of Alkaloids Content

Take three portions of approximately 1 g of the coarse powder of this product, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer). Titrate with 1 mmol·L−1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of alcohol extract contains 0.028±0.007 g of alkaloids.

(4) Determination of Coumarins Content

It is determined that the coumarins content is 1% to 10%.

4. Studies on Antitumor Activity of Paliurus ramosissimus (Lour.) Poir. Leaf Alcohol Extract at Three Polar Parts Extract Paliurus ramosissimus (Lour.) Poir. leaf alcohol extract with petroleum ether, ethyl acetate and n-butanol in sequence, recover solvents and freeze dry to obtain extracts at three polar parts, and dissolve in isopropanol. Take a variety of tumor cells in logarithmic growth phase (tumor cell lines used are the followings: cervical carcinoma cell line Hela; human hepatoma cell line SMMC-7721; human lung carcinoma cell line A549; human colon carcinoma cell line Caco-2; leukemia cell line K562; gastric carcinoma cell line MGC-803;), centrifuge at 2000 rpm for 5 min, adjust precipitate cell concentration of cell suspension to $1\times10^5$ cells/ml with corresponding culture medium containing 10% fetal bovine serum, and seed cells in 96-well culture plates. To each well, add 200 μl of cell suspension, respectively add sterile extract solution of certain concentration to make the final concentration of extract in each well is 0.002, 0.01, 0.02, 0.04, 0.05, 0.08, 0.1, 0.2 mg/ml, mix well, place in 37° C., 5% $CO_2$ incubator for 24 h, precipitate the culture, wash twice with PBS, to each well, add 20 μl of 5 mg/ml MTT phosphate buffer and 150 μl of culture medium, culture under the same conditions for 4 h, and then terminate the culture. Centrifuge at 2000 rpm for 5 min, then discard the culture medium in wells, to each well, add 150 μl of DMSO, shake for 10 min so that the formed formazan particles are fully dissolved, and determine absorbance with microplate reader. Select 570 nm as the measurement wavelength. Calculate IC50 of the extract to tumor cells. The results are shown in Table 2. The results are that Paliurus ramosissimus (Lour.) Poir. leaf alcohol extract at petroleum ether part and ethyl acetate part have good anti-tumor activity, especially extract at ethyl acetate part has better activity, while IC50 of extract at n-butanol part cannot be calculated within the experiment concentration range. We further study the ethyl acetate part.

TABLE 2

Inhibition effects of *Paliurus ramosissimus* (Lour.) Poir. extract at different polar part on tumor cells:

| Cell line | Petroleum ether part | Ethyl acetate part | N-butanol part |
|---|---|---|---|
| Hela | 0.0492 mg/ml | 0.0139 mg/ml | — |
| SMMC-7721 | 0.0993 mg/ml | 0.0365 mg/ml | — |
| A549 | 0.0142 mg/ml | 0.0075 mg/ml | — |
| Caco-2 | 0.0545 mg/ml | 0.0778 mg/ml | — |
| MGC-803 | 0.0702 mg/ml | 0.0305 mg/ml | — |

5. Studies on Effects of Ethyl Acetate Polar Part on Mice Bearing Ehrlich Ascites Tumor Inhibition of mice transplanted tumor S180:

Take Kunming mice, subcutaneously inject 0.2 ml of S180 suspension (about $1 \times 10^6$ tumor cells) in a routine way at the right anterior lobe. 24 hours after injection, mice are randomly grouped and numbered. There are 10 mice in the control groups, and 10 mice each in test groups of high dose, middle dose, and low dose. Mice in each group receive drugs via intragastric administration once a day for a total of 14 times. In positive control group, cyclophosphamide (85 mg/kg) is given daily, and the dose, frequency, time are identical with the test groups. 24 hours after the last administration, sacrifice the animals, weigh body weight, completely remove tumor lump, weigh, and calculate tumor inhibition rate, the results are shown in Table 3.

TABLE 3

Effects of ethyl acetate polar part on mice bearing Ehrlich ascites tumor

| Group | Control group | Ethyl acetate polar part (low dose) | Ethyl acetate polar part (middle dose) | Ethyl acetate polar part (high dose) |
|---|---|---|---|---|
| Tumor inhibition rate | 38.45 ± 3.62% | 13.85 ± 4.59% | 40.76 ± 5.40% | 76.13 ± 8.32%* |

*Compared with the control group, $P < 0.05$; the difference is statistically significant.

II. The Antitumor Activity of *Paliurus ramosissimus* (Lour.) Poir. Whole Plant Extract

Embodiment 1

Take 1 kg of *Paliurus ramosissimus* (Lour.) Poir. whole plant, add 95% ethanol of 8 times the weight, soak for one day, then crush, add 95% ethanol of 10 times the weight, soak for 2 days, collect the extract liquid, recover ethanol at 50° C. under reduced pressure until no ethanol smell and dry to obtain *Paliurus ramosissimus* (Lour.) Poir. ethanol extract.

Embodiment 2

Take 1 kg of *Paliurus ramosissimus* (Lour.) Poir. stems and leaves, add 95% ethanol of 10 times the weight, soak for one day, then crush, add 95% ethanol of 10 times the weight for reflux extraction, collect the extract liquid, recover ethanol at 60° C. under reduced pressure until no ethanol smell and dry to obtain *Paliurus ramosissimus* (Lour.) Poir. ethanol extract. Disperse *Paliurus ramosissimus* (Lour.) Poir. ethanol extract in water, and extract with petroleum ether and ethyl acetate in sequence, to obtain petroleum ether extract and ethyl acetate extract.

Embodiment 3

Take 1 kg of *Paliurus ramosissimus* (Lour.) Poir. whole plant, add methanol of 10 times the weight, soak for one day, then crush, add methanol of 8 times the weight, soak for 2 days, collect the extract liquid, recover methanol at 40° C. under reduced pressure, and dry to obtain *Paliurus ramosissimus* (Lour.) Poir. methanol extract. Disperse *Paliurus ramosissimus* (Lour.) Poir. methanol extract in water, and extract with petroleum ether and ethyl acetate in sequence, to obtain petroleum ether extract and ethyl acetate extract.

Embodiment 4

Take three portions of 0.1 g of *Paliurus ramosissimus* (Lour.) Poir. petroleum ether extract in Embodiment 2, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of *Paliurus ramosissimus* (Lour.) Poir extract contains 23 mg of triterpenoids.

Take three portions of 0.1 g of *Paliurus ramosissimus* (Lour.) Poir. petroleum ether extract in Embodiment 2, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance at wavelength of 510 nm, and calculate total flavonoids content in sample test solution (flavonoids as rutin). The calculation has showed that 1 g of *Paliurus ramosissimus* (Lour.) Poir. extract contains 103 mg of flavonoids.

Take three portions of 0.1 g of *Paliurus ramosissimus* (Lour.) Poir. petroleum ether extract in Embodiment 2, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer).

Titrate with 1 mmol·L−1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of *Paliurus ramosissimus* (Lour.) Poir. extract contains 21 g of alkaloids.

Take three portions of 0.1 g of *Paliurus ramosissimus* (Lour.) Poir. petroleum ether extract in Embodiment 2, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add 70% ethanol to the mark, and shake well. Precisely pipette 3 ml, and transfer to 25-ml volumetric flasks, determine absorbance at wavelength of 340 nm, and calculate total coumarins content in sample test solution (coumarins as umbelliferone). The calculation has showed that 1 g of *Paliurus ramosissimus* (Lour.) Poir. extract contains 10.2 mg of total coumarins.

Embodiment 5

Take three portions of 0.1 g of *Paliurus ramosissimus* (Lour.) Poir. ethyl acetate extract in Embodiment 2, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of *Paliurus ramosissimus* (Lour.) Poir extract contains 108 g of triterpenoids.

Take three portions of 0.1 g of *Paliurus ramosissimus* (Lour.) Poir. ethyl acetate extract in Embodiment 2, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance at wavelength of 510 nm, and calculate total flavonoids content in sample test solution (flavonoids as rutin). The calculation has showed that 1 g of *Paliurus ramosissimus* (Lour.) Poir. extract contains 497 mg of flavonoids.

Take three portions of 0.1 g of *Paliurus ramosissimus* (Lour.) Poir. ethyl acetate extract in Embodiment 2, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer). Titrate with 1 mmol·L−1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of *Paliurus ramosissimus* (Lour.) Poir. extract contains 107 mg of alkaloids.

Take three portions of 0.1 g of *Paliurus ramosissimus* (Lour.) Poir. ethyl acetate extract in Embodiment 2, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add 70% ethanol to the mark, and shake well. Precisely pipette 3 ml, and transfer to 25-ml volumetric flasks, determine absorbance at wavelength of 340 nm, and Calculate total coumarins content in sample test solution (coumarins as umbelliferone). The calculation has showed that 1 g of *Paliurus ramosissimus* (Lour.) Poir. extract contains 186 mg of coumarins.

1. Studies on In Vitro Anti-Tumor Activity of *Paliurus ramosissimus* (Lour.) Poir. Ethanol Extract Take a variety of tumor cells in logarithmic growth phase (tumor cell lines used are the followings: cervical carcinoma cell line Hela; human hepatoma cell line SMMC-7721; human lung carcinoma cell line A549; human colon carcinoma cell line Caco-2; leukemia cell line K562; gastric carcinoma cell line MGC-803;), centrifuge at 2000 rpm for 5 min, adjust precipitate cell concentration of cell suspension to $1\times10^5$ cells/ml with corresponding culture medium containing 10% fetal bovine serum, and seed cells in 96-well culture plates. To each well, add 200 μl of cell suspension, respectively add sterile extract solution of certain concentration to make the final concentration of extract in each well is 0.02, 0.1, 0.2, 0.4, 0.5, 0.8, 1.0, 2.0 mg/ml, mix well, place in 37° C., 5% $CO_2$ incubator for 24 h, precipitate the culture, wash twice with PBS, to each well, add 20 μl of 5 mg/ml MTT phosphate buffer and 150 μl of culture medium, culture under the same conditions for 4 h, and then terminate the culture. Centrifuge at 2000 rpm for 5 min, then discard the culture medium in wells, to each well, add 150 μl of DMSO, shake for 10 min so that the formed formazan particles are fully dissolved, and select 570 nm as the measurement wavelength, determine absorbance with microplate reader. Calculate IC50 of the *Paliurus ramosissimus* (Lour.) Poir. ethanol extract in embodiment 1 to tumor cells. The results are shown in Table 4. The results have showed that, *Paliurus ramosissimus* (Lour.) Poir whole plant extract has good anti-tumor effect.

TABLE 4

The inhibition effects of *Paliurus ramosissimus* (Lour.) Poir. ethanol extract on different tumor cells

| Cell line | *Paliurus ramosissimus* (Lour.) Poir. ethanol extract |
| --- | --- |
| Hela | 0.0216 mg/ml |
| SMMC-7721 | 0.1452 mg/ml |
| A549 | 0.0101 mg/ml |
| Caco-2 | 0.0875 mg/ml |
| MGC-803 | 0.1862 mg/ml |

2. Studies on In Vitro Anti-Tumor Activity of 3 *Paliurus ramosissimus* (Lour.) Poir. Extracts in Embodiment 2

Extract *Paliurus ramosissimus* (Lour.) Poir. ethanol extract in Embodiment 1 with petroleum ether, ethyl acetate and n-butanol in sequence, recover solvents and freeze dry to obtain *Paliurus ramosissimus* (Lour.) Poir. petroleum ether extract, ethyl acetate extract and n-butanol extract, and dissolve in isopropanol. Take a variety of tumor cells in logarithmic growth phase (tumor cell lines used are the followings: cervical carcinoma cell line Hela; human hepatoma cell line SMMC-7721; human lung carcinoma cell line A549; human colon carcinoma cell line Caco-2; leukemia cell line K562; gastric carcinoma cell line MGC-803;), centrifuge at 2000 rpm for 5 min, adjust precipitate cell concentration of cell suspension to $1\times10^5$ cells/ml with corresponding culture medium containing 10% fetal bovine serum, and seed cells in 96-well culture plates. To each well, add 200 μl of cell suspension, respectively add sterile extract solution of certain concentration to make the final concentration of extract in each well is 0.002, 0.01, 0.02, 0.04, 0.05, 0.08, 0.1, 0.2 mg/ml, mix well, place in 37° C., 5% $CO_2$ incubator for 24 h, precipitate the culture, wash twice with PBS, to each well, add 20 μl of 5 mg/ml MTT phosphate buffer and 150 μl of culture medium, culture under the same conditions for 4 h, and then terminate the culture. Centrifuge at 2000 rpm for 5 min, then discard the culture medium in wells, to each well, add 150 μl of DMSO, shake for 10 min so that the formed formazan particles are fully dissolved, and select 570 nm as the measurement wavelength, determine absorbance with microplate reader. Calculate IC50 of the extract to tumor cells. The results are shown in Table 5. The results are that *Paliurus ramosissimus* (Lour.) Poir. petroleum ether extract and ethyl acetate extract have good anti-tumor activity, especially extract at ethyl acetate part has better activity, while IC50 of n-butanol extract cannot be calculated within the experiment concentration range.

TABLE 5

The inhibition effects of different *Paliurus ramosissimus* (Lour.) Poir. extracts on tumor cells

| Cell line | Petroleum ether extract | Ethyl acetate extract | N-butanol extract |
|---|---|---|---|
| Hela | 0.0357 mg/ml | 0.0102 mg/ml | — |
| SMMC-7721 | 0.1242 mg/ml | 0.0357 mg/ml | — |
| A549 | 0.0156 mg/ml | 0.0064 mg/ml | — |
| Caco-2 | 0.0915 mg/ml | 0.0623 mg/ml | — |
| MGC-803 | 0.0812 mg/ml | 0.0487 mg/ml | — |

"—": IC50 cannot be calculated within the experiment concentration range

3. Effects of *Paliurus ramosissimus* (Lour.) Poir. Ethanol, Methanol, Petroleum Ether and Ethyl Acetate Extracts on Mice Bearing S180

Choose mice which are in good health conditions and received S180 tumor injection 8 days ago, disinfect abdominal skin, draw ascites, mix with normal saline as ratio of 1:4 (ascites volume: normal saline volume) to make suspension. Take 82 male Kunming mice, weighing 18-20 g, randomly divide into 7 groups with stratification of body weight, namely model control group (0.5% mucilage tragacanth), positive control group (cyclophosphamide, CTX), ethyl acetate extract low-dose group, ethyl acetate extract high-dose group, ethanol extract group, methanol extract group, and petroleum ether extract group. In all groups, subcutaneously inject 0.2 ml of the aforementioned suspension at the right anterior lobe. 2 hours after injection, mice in control group and drug groups receive test substance or suspension via intragastric administration once a day for 14 consecutive days. In positive control group, CTX is administered intraperitoneally once every other day for a total of 7 times. 24 h after the last administration, sacrifice the mice by cervical dislocation, remove tumor lump, weigh, and calculate inhibition rate ((1−average tumor weight in the experimental group/average tumor weight in the model control group)*100%). The results are shown in Table 6.

TABLE 6

Effect of *Paliurus ramosissimus* (Lour.) Poir. whole plant extract on mice bearing S180 ($\bar{x} \pm s$)

| Group | Number of animals | Dose | Tumor weight (g) | Tumor inhibition rate (%) |
|---|---|---|---|---|
| Model control | 11 | — | 1.20 ± 0.45 | — |
| Positive control (ctx) | 9 | 40 mg/kg | 0.35 ± 0.58** | 70.8 |
| Ethyl acetate extract low-dose | 12 | 0.4 g/kg | 1.14 ± 0.46 | 5.0 |
| Ethyl acetate extract high-dose | 12 | 1.6 g/kg | 0.34 ± 0.43** | 71.7 |
| Methanol extract | 12 | 4.8 g/kg | 0.57 ± 0.45** | 52.5 |
| Petroleum ether extract | 12 | 4.8 g/kg | 0.39 ± 0.23** | 67.5 |
| Ethanol extract | 12 | 4.8 g/kg | 0.44 ± 0.29** | 63.3 |

*Compared with the model control group, *P < 0.05, **P < 0.01

Experimental results have showed that intraperitoneal administration of 1.6 g/kg of *Paliurus ramosissimus* (Lour.) Poir. whole plant ethyl acetate extract can significantly inhibit the growth of S180 in mice, and potency of 1.6 g/kg dose is similar to intraperitoneal administration of 40 mg/kg of cyclophosphamide every other day; 4.8 g/kg of ethanol, methanol, petroleum ether extracts can also effectively reduce tumor weight, and the tumor inhibition rate is over 50%, suggesting that the four extracts have good anti-tumor activity.

4. Effects of *Paliurus ramosissimus* (Lour.) Poir. Ethanol, Methanol, Petroleum Ether and Ethyl Acetate Extracts on Mice Bearing Ehrlich Ascites Tumor Choose mice which are in good health conditions and received Ehrlich ascites tumor injection 8 days ago, disinfect abdominal skin, draw ascites, mix with normal saline to $4\times10^6$ ml for future use. Take 82 male Kunming mice, weighing 18-20 g, randomly divide into 7 groups with stratification of body weight, namely model control group (0.5% mucilage tragacanth), positive control group (cyclophosphamide, CTX), ethyl acetate extract low-dose group, ethyl acetate extract high-dose group, ethanol extract group, methanol extract group, and petroleum ether extract group. In all groups, subcutaneously inject 0.2 ml of the aforementioned suspension at the right anterior lobe. 2 hours after injection, mice in control group and drug groups receive test substance or suspension via intragastric administration once a day, administer continuously until the animal is dying. In positive control group, CTX is administered intraperitoneally once every other day for a total of 7 times. When the animal is dying, sacrifice it by cervical dislocation; the day of dying is calculated as survival time; after death, weigh, exhaust ascites, weigh again, and the difference is the weight of ascites. The results are shown in Table 7.

TABLE 7

Effect of *Paliurus ramosissimus* (Lour.) Poir. whole plant extract on mice bearing Ehrlich ascites tumor ($\bar{x} \pm s$)

| Group | Dose | Number of animals | Survival time (Day) | Weight of ascites |
|---|---|---|---|---|
| Model control | — | 12 | 16.3 ± 2.5 | 21.4 ± 1.8 |
| Positive control (ctx) | 40 mg/kg | 12 | 17.2 ± 2.3 | 15.9 ± 1.5** |
| Ethyl acetate extract low-dose | 0.4 g/kg | 12 | 19.9 ± 3.9* | 17.3 ± 1.8** |
| Ethyl acetate extract high-dose | 1.6 g/kg | 12 | 20.5 ± 2.7** | 14.2 ± 2.0** |
| Methanol extract | 4.8 g/kg | 12 | 19.0 ± 3.1* | 16.9 ± 2.5** |
| Petroleum ether extract | 4.8 g/kg | 12 | 19.6 ± 2.2** | 15.5 ± 1.1** |
| Ethanol extract | 4.8 g/kg | 12 | 20.1 ± 2.9** | 17.2 ± 2.2** |

Compared with the model control group, *P < 0.05, **P < 0.01

Experimental results have showed that intraperitoneal administration of 0.4 g/kg and above of *Paliurus ramosissimus* (Lour.) Poir. whole plant ethyl acetate extract can significantly inhibit the growth of Ehrlich ascites tumor in mice, and prolong animal survival time; the potency of 1.6 g/kg dose is similar to cyclophosphamide on inhibiting the amount of ascites, but the latter cannot prolong animal survival time, suggesting that certain unique advantages; 4.8 g/kg of ethanol, methanol, petroleum ether extracts can also effectively prolong survival time, inhibit ascites formation, suggesting that the four extracts have good anti-tumor activity.

5. Effects of *Paliurus ramosissimus* (Lour.) Poir. Ethyl Acetate Extract in Combination of Paclitaxel and Cinobufotalin on Mice Bearing S180

Choose mice which are in good health conditions and received S180 tumor injection 8 days ago, disinfect abdominal skin, draw ascites, mix with normal saline as ratio of 1:4 (ascites volume:normal saline volume) to make suspension. Take 84 male Kunming mice, weighing 18-20 g, randomly divide into 7 groups with stratification of body weight, namely model control group (0.5% mucilage tragacanth), positive control group (cyclophosphamide, CTX), ethyl acetate extract group, paclitaxel group, cinobufotalin group, in combination with paclitaxel group, in combination with cinobufotalin group. In all groups, subcutaneously inject 0.2 ml of the aforementioned suspension at the right anterior lobe. 2 hours after injection, mice in control group and drug groups receive test substance or suspension via intragastric or intravenous administration once a day for 14 consecutive days. In positive control group, CTX is administered intraperitoneally once every other day for a total of 7 times. 24 h after the last administration, sacrifice the mice by cervical dislocation, remove tumor lump, weigh, and calculate inhibition rate ((1−average tumor weight in the experimental group/average tumor weight in the model control group) *100%). The results are shown in Table 8.

TABLE 8

Effect of *Paliurus ramosissimus* (Lour.) Poir. whole plant ethyl acetate extract in combination of paclitaxel and cinobufotalin on mice bearing S180 ($\bar{x} \pm s$)

| Group | Number of animals | Dose | Tumor weight (g) | Tumor inhibition rate (%) |
|---|---|---|---|---|
| Model control | 11 | — | 1.30 ± 0.55 | — |
| Positive control (CTX) | 12 | 40 mg/kg | 0.48 ± 0.41** | 63.1 |
| Ethyl acetate extract | 12 | 0.4 g/kg | 1.04 ± 0.40 | 20.0 |
| Paclitaxel | 12 | 5 mg/kg | 0.85 ± 0.38* | 34.6 |
| In combination with paclitaxel | 12 | Ethyl acetate extract 0.4 g/kg + paclitaxel 5 mg/kg | 0.52 ± 0.26**@ | 60.0 |
| Cinobufotalin | 12 | 1 ml/kg | 0.73 ± 0.42* | 43.8 |
| In combination with cinobufotalin | 12 | Ethyl acetate extract 0.4 g/kg + cinobufotalin 1 ml/kg | 0.37 ± 0.18**# | 71.5 |

Compared with the model control group, *P < 0.05, **P < 0.01;
Compared with the paclitaxel group, @P < 0.05;
Compared with the cinobufotalin group, #P < 0.05;

Experimental results have showed that intraperitoneal administration of 0.4 g/kg of *Paliurus ramosissimus* (Lour.) Poir. whole plant ethyl acetate extract does not have significant inhibition effect on the growth of S180 in mice, while 5 mg/kg of paclitaxel and 1 ml/kg of cinobufotalin show certain effects. However, the combination of the same dose of *Paliurus ramosissimus* (Lour.) Poir. whole plant ethyl acetate extract and 5 mg/kg of paclitaxel and 1 ml/kg of cinobufotalin can significantly improve the inhibition rate of paclitaxel, suggesting that the combination of *Paliurus ramosissimus* (Lour.) Poir. whole plant extract and other antitumor drugs can improve the efficacy of these drugs.

III. Antifibrotic Activity of *Paliurus ramosissimus* (Lour.) Poir. Extract

Embodiment 1

Take 1 kg of *Paliurus ramosissimus* (Lour.) Poir. whole plant, add 95% ethanol of 8 times the weight, soak for one day, then crush, add 95% ethanol of 10 times the weight, soak for 2 days, collect the extract liquid, recover ethanol at 50° C. under reduced pressure until no ethanol smell to obtain *Paliurus ramosissimus* (Lour.) Poir. ethanol extract.

Embodiment 2

Take 1 kg of *Paliurus ramosissimus* (Lour.) Poir. stems and leaves, add 95% ethanol of 10 times the weight, soak for one day, then crush, add 95% ethanol of 10 times the weight for reflux extraction, collect the extract liquid, recover ethanol at 60° C. under reduced pressure until no ethanol smell to obtain *Paliurus ramosissimus* (Lour.) Poir. ethanol extract. Disperse *Paliurus ramosissimus* (Lour.) Poir. ethanol extract in water, and extract with petroleum ether and ethyl acetate in sequence, to obtain petroleum ether extract and ethyl acetate extract.

Embodiment 3

Take 1 kg of *Paliurus ramosissimus* (Lour.) Poir. whole plant, add methanol of 10 times the weight, soak for one day, then crush, add methanol of 8 times the weight, soak for 2 days, collect the extract liquid, recover methanol at 40° C. under reduced pressure, and dry to obtain *Paliurus ramosissimus* (Lour.) Poir. methanol extract. Disperse *Paliurus ramosissimus* (Lour.) Poir. methanol extract in water, and extract with petroleum ether and ethyl acetate in sequence, to obtain petroleum ether extract and ethyl acetate extract.

Embodiment 4

Take three portions of 0.1 g of *Paliurus ramosissimus* (Lour.) Poir. petroleum ether extract in Embodiment 2, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of *Paliurus ramosissimus* (Lour.) Poir extract contains 23 g of triterpenoids.

Take three portions of 0.1 g of *Paliurus ramosissimus* (Lour.) Poir. petroleum ether extract in Embodiment 2, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance at wavelength of 510 nm, and calculate total flavonoids content in sample test solution (flavonoids as rutin). The calculation has showed that 1 g of *Paliurus ramosissimus* (Lour.) Poir. extract contains 103 mg of flavonoids.

Take three portions of 0.1 g of *Paliurus ramosissimus* (Lour.) Poir. petroleum ether extract in Embodiment 2, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer). Titrate with 1 mmol·L-1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of *Paliurus ramosissimus* (Lour.) Poir. extract contains 21 g of alkaloids.

Take three portions of 0.1 g of *Paliurus ramosissimus* (Lour.) Poir. petroleum ether extract in Embodiment 2, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add 70% ethanol to the mark, and shake well. Precisely pipette 3 ml, and transfer to 25-ml volumetric flasks, determine absorbance at wavelength of 340 nm, and Calculate total coumarins content in sample test solution (coumarins as umbelliferone). The calculation has showed that 1 g of *Paliurus ramosissimus* (Lour.) Poir. extract contains 10.2 mg of total coumarins.

Embodiment 5

Take three portions of 0.1 g of *Paliurus ramosissimus* (Lour.) Poir. ethyl acetate extract in Embodiment 2, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of *Paliurus ramosissimus* (Lour.) Poir extract contains 108 g of triterpenoids.

Take three portions of 0.1 g of *Paliurus ramosissimus* (Lour.) Poir. ethyl acetate extract in Embodiment 2, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance at wavelength of 510 nm, and calculate total flavonoids content in sample test solution (flavonoids as rutin). The calculation has showed that 1 g of *Paliurus ramosissimus* (Lour.) Poir. extract contains 497 mg of total flavonoids.

Take three portions of 0.1 g of *Paliurus ramosissimus* (Lour.) Poir. ethyl acetate extract in Embodiment 2, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer). Titrate with 1 mmol·L-1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of *Paliurus ramosissimus* (Lour.) Poir. extract contains 107 mg of alkaloids.

Take three portions of 0.1 g of *Paliurus ramosissimus* (Lour.) Poir. ethyl acetate extract in Embodiment 2, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add 70% ethanol to the mark, and shake well. Precisely pipette 3 ml, and transfer to 25-ml volumetric flasks, determine absorbance at wavelength of 340 nm, and calculate total coumarins content in sample test solution (coumarins as umbelliferone). The calculation has showed that 1 g of *Paliurus ramosissimus* (Lour.) Poir. extract contains 186 mg of coumarins.

1. Effect on Liver Fibrosis in Rats

Take 60 SD rats (200-240 g, male), randomly divide into blank control group (0.5% mucilage tragacanth), model control group (0.5% mucilage tragacanth), positive control group (dexamethasone, 1 mg/kg), *Paliurus ramosissimus* (Lour.) Poir. extract (prepared according to Embodiment 1) low-dose group (0.4 g/kg), *Paliurus ramosissimus* (Lour.) Poir. extract middle-dose group (0.8 g/kg), and *Paliurus ramosissimus* (Lour.) Poir. extract high-dose group (1.6 g/kg) with stratification of body weight. Except the blank control group, rats in other groups receive subcutaneous injection of 1 ml/kg of 40% carbon tetrachloride in vegetable oil solution, 2 times a week for 3 consecutive months, while receiving high-fat diet and 5% ethanol aqueous solution. Test substance is given via intragastric administration once daily for 3 consecutive months. On the next day after drug administration, draw abdominal aortic blood, separate plasma, determine the levels of alanine aminotransferase (ALT), III procollagen (PC-III), hyaluronic acid (HA) and laminin (LH); the sacrifice the animals, and take the liver for pathological examination. Serum biochemical test results are shown in Table 9.

TABLE 9

Effect of *Paliurus ramosissimus* (Lour.) Poir. extract on experimental hepatic fibrosis rat liver and blood biochemical indices (n = 10, $\bar{x} \pm s$)

| Group | ALT (U/L) | PC-III (µg/L) | HA (µg/L) | LN (µg/L) |
| --- | --- | --- | --- | --- |
| Normal control | 43 ± 4** | 9.5 ± 1.7** | 131 ± 29** | 12 ± 2** |
| Model control | 678 ± 123 | 32.2 ± 6.9 | 319 ± 71 | 86 ± 19 |
| Positive Control | 456 ± 98** | 20.8 ± 3.1** | 280 ± 54 | 62 ± 20* |
| *Paliurus ramosissimus* (Lour.) Poir. Extract (0.4 g/kg) | 617 ± 107 | 30.5 ± 6.2 | 289 ± 62 | 80 ± 23 |
| *Paliurus ramosissimus* (Lour.) Poir. extract (0.8 g/kg) | 412 ± 126** | 25.1 ± 4.2* | 263 ± 69 | 59 ± 17* |
| *Paliurus ramosissimus* (Lour.) Poir. Extract (1.6 g/kg) | 335 ± 138** | 18.5 ± 4.8** | 217 ± 58** | 41 ± 9** |

Compared with the model control group, *P < 0.05, **P < 0.01

The results have showed that, compared with the model group, 0.8 g/kg and 1.6 g/kg of *Paliurus ramosissimus* (Lour.) Poir. extract have a protective role in carbon tetrachloride-induced experimental fibrosis rat liver injury; particularly in higher dose, each index is improved significantly.

Pathological examination has showed that liver cells of rats in the model group show obvious water degeneration, obvious liver necrosis and fatty degeneration, with obvious liver fibrosis manifestations; compared to the model group, in *Paliurus ramosissimus* (Lour.) Poir. extract high-dose group and middle-dose group, the degree of liver cell water degeneration and fatty degeneration is significantly lower, suggesting that it has good inhibitory effect on liver fibrosis.

2. Effect on Pulmonary Fibrosis in Rats

Take 60 SD rats (200-240 g, male), randomly divide into sham operation control group (0.5% mucilage tragacanth), model control group (0.5% mucilage tragacanth), positive control group (dexamethasone, 1 mg/kg), *Paliurus ramosissimus* (Lour.) Poir. extract (prepared according to Embodiment 1) low-dose group (0.4 g/kg), *Paliurus ramosissimus* (Lour.) Poir. extract middle-dose group (0.8 g/kg), and *Paliurus ramosissimus* (Lour.) Poir. extract high-dose group (1.6 g/kg) with stratification of body weight. All animals receive trachea separation under anesthesia by intraperitoneal injection of 10% chloral hydrate (350 mg/kg). Except the sham operation control group, rats in other groups receive injection of 5 mg/kg of bleomycin in 0.4 ml of normal saline solution, while rats in sham operation control group receive normal saline solution only. From the next day after surgery, test substance is given daily for 30 consecutive days. Sacrifice the animals by cervical dislocation, and take the lungs; some organs are homogenized for hydroxyproline content determination, and some are for pathological examination. The results of determined hydroxyproline content in lung tissue are shown in Table 10.

TABLE 10

The change of hydroxyproline content in the lungs of rats in each group (n = 10, $\bar{x} \pm s$)

| Group | Hydroxyproline content (mg/gpro) |
| --- | --- |
| Sham operation control | 10.3 ± 3.8** |
| Model control | 18.4 ± 5.0 |
| Positive Control | 13.6 ± 3.3* |
| *Paliurus ramosissimus* (Lour.) Poir. Extract (0.4 g/kg) | 16.5 ± 4.7 |
| *Paliurus ramosissimus* (Lour.) Poir. Extract (0.8 g/kg) | 14.1 ± 6.2* |
| *Paliurus ramosissimus* (Lour.) Poir. Extract (1.6 g/kg) | 12.3 ± 3.7* |

Compared with the model control group, *P < 0.05, **P < 0.01

The results have showed that, compared with the model group, 0.8 g/kg and 1.6 g/kg of *Paliurus ramosissimus* (Lour.) Poir. extract effectively reduce hydroxyproline content in the lung of model rats, suggesting that it has good inhibition effect of pulmonary fibrosis.

Pathological examination tests have showed that, rats in the model group appear obvious pulmonary fibrosis, with manifestation of a large number of interstitial lung fibroblasts, a large number of fibrous connective tissue deposition, structural damage in alveolar cells, and some alveolar space disappearance; compared with the model group, in *Paliurus ramosissimus* (Lour.) Poir. extract each dose group, fibrous connective tissue deposition in rats is less, and interstitial lung fibroblasts are also less, while the high-dose group is more significant, suggesting that the extract is a potential treatment of pulmonary fibrosis.

3. Effect of *Paliurus ramosissimus* (Lour.) Poir. Extract in Combination with Polyene Phosphatidylcholine on Liver Fibrosis in Rats Take 60 SD rats (200-240 g, male), randomly divide into blank control group, model control group, positive control group (dexamethasone, 1 mg/kg), *Paliurus ramosissimus* (Lour.) Poir. extract group (prepared according to Embodiment 1, 0.8 g/kg), Polyene phosphatidylcholine group, drug combination group (*Paliurus ramosissimus* (Lour.) Poir. Extract 0.8 g/kg+ Polyene phosphatidylcholine 1 ml/kg) with stratification of body weight. Except the blank control group, rats in other groups receive subcutaneous injection of 1 ml/kg of 40% carbon tetrachloride in vegetable oil solution, 2 times a week for 3 consecutive months, while receiving high-fat diet and 5% ethanol aqueous solution. Test substance is given via intragastric administration once daily for 3 consecutive months. On the next day after drug administration, draw abdominal aortic blood, separate plasma, determine the levels of alanine aminotransferase (ALT), III procollagen (PC-III), hyaluronic acid (HA) and laminin (LH); the sacrifice the animals, and take the liver for pathological examination. Serum biochemical test results are shown in Table 11.

TABLE 11

Effect of drug combination on experimental hepatic fibrosis rat liver and blood biochemical indices (n = 10, $\bar{x} \pm s$)

| Group | ALT (U/L) | PC-III (μg/L) | HA (μg/L) | LN (μg/L) |
|---|---|---|---|---|
| Normal control | 42 ± 3** | 9.7 ± 1.9** | 129 ± 32** | 11 ± 4** |
| Model control | 684 ± 114 | 31.7 ± 8.0 | 310 ± 63 | 87 ± 21 |
| Positive control | 478 ± 90** | 20.6 ± 3.8** | 285 ± 57 | 65 ± 23* |
| *Paliurus ramosissimus* (Lour.) Poir. Extract | 423 ± 98** | 24.5 ± 3.9* | 271 ± 60 | 60 ± 18** |
| Polyene phosphatidylcholine | 443 ± 130** | 27.0 ± 4.8 | 284 ± 78 | 63 ± 18* |
| Drug combination | 315 ± 102**# | 18.6 ± 5.1**## | 186 ± 67**## | 47 ± 11**# |

Compared with the model control group, *P < 0.05, **P < 0.01;
compared with polyene phosphatidylcholine group, #P < 0.05, ##P < 0.01

4. Effect of *Paliurus ramosissimus* (Lour.) Poir. Extract in Combination with Ligustrazine on Pulmonary Fibrosis in Rats Take 60 SD rats (200-240 g, male), randomly divide into sham operation control group, model control group, positive control group (dexamethasone, 1 mg/kg), *Paliurus ramosissimus* (Lour.) Poir. extract group (prepared according to Embodiment 1, 0.8 g/kg·op), Ligustrazine (40 mg/kg, ip) and drug combination group (*Paliurus ramosissimus* (Lour.) Poir. Extract 0.8 g/kg, op; Ligustrazine injection 40 mg/kg, ip) with stratification of body weight. All animals receive trachea separation under anesthesia by intraperitoneal injection of 10% chloral hydrate (350 mg/kg). Except the sham operation control group, rats in other groups receive injection of 5 mg/kg of bleomycin in 0.4 ml of normal saline solution, while rats in sham operation control group receive normal saline solution only. The next day after the surgery, give the test substance via intragastric administration or injection administration, test substance is given daily for 30 consecutive days. Sacrifice the animals by cervical dislocation, and take the lungs; some organs are homogenized for hydroxyproline content determination, and some are for pathological examination. The results of determined hydroxyproline content in lung tissue are shown in Table 12.

TABLE 12

Effect of drug combination on hydroxyproline in the lungs of rats (n = 10, $\bar{x} \pm s$)

| Group | Hydroxyproline content (mg/gpro) |
|---|---|
| Sham operation control | 10.1 ± 3.4** |
| Model control | 17.9 ± 4.3 |

TABLE 12-continued

Effect of drug combination on hydroxyproline in the lungs of rats (n = 10, $\bar{x} \pm s$)

| Group | Hydroxyproline content (mg/gpro) |
|---|---|
| Positive control | 13.4 ± 3.7* |
| *Paliurus ramosissimus* (Lour.) Poir. Extract | 12.9 ± 4.9* |
| Ligustrazine | 14.6 ± 5.7 |
| Drug combination | 9.8 ± 2.9**# |

Compared with the model control group, *P < 0.05, **P < 0.01;
Compared with the Ligustrazine group, #P < 0.05

The results have showed that, 40 mg/kg of ligustrazine alone has no significant efficacy on experimental pulmonary fibrosis, while drug combination effectively reduces hydroxyproline content in lungs in model rats, which has significant differences when being compared with 40 mg/kg of ligustrazine, suggesting that *Paliurus ramosissimus* (Lour.) Poir. extract can effectively improve the efficacy of other pulmonary fibrosis therapeutic agents.

IV. Antifungal Activity of *Paliurus ramosissimus* (Lour.) Poir. Extract (I) Embodiment Preparation of *Paliurus ramosissimus* (Lour.) Poir. Extract 1. Preparation of *Paliurus ramosissimus* (Lour.) Poir. Ethanol Extract (1) Take 1 kg of the whole plant of fresh *Paliurus ramosissimus* (Lour.) Poir., add 95% (volume concentration) ethanol of 8 times of the volume of *Paliurus ramosissimus* (Lour.) Poir., soak for 1-2 days, crush leaves, roots and stems, add 95% ethanol of 12 times of the volume of *Paliurus ramosissimus* (Lour.) Poir., soak for 3 days, collect the extract liquid, recover ethanol under reduced pressure, and freeze-dry the concentrated to obtain *Paliurus ramosissimus* (Lour.) Poir. ethanol extract.

(2) Take 1 kg of the whole plant (or any part) of fresh *Paliurus ramosissimus* (Lour.) Poir., crush, add 95% ethanol of 8 times of the volume of *Paliurus ramosissimus* (Lour.) Poir., reflux to extract 3 times, collect the extract liquid, recover ethanol under reduced pressure, and freeze-dry the concentrated to obtain *Paliurus ramosissimus* (Lour.) Poir. ethanol extract.

(3) Take 1 kg of the whole plant of fresh *Paliurus ramosissimus* (Lour.) Poir. (roots, stems, leaves, etc.), freeze-dry and then crush (or crush and then freeze-dry), add 95% ethanol of 10 times of the volume of *Paliurus ramosissimus* (Lour.) Poir., reflux to extract 3 times, collect the extract liquid, recover ethanol under reduced pressure, and freeze-dry the concentrated to obtain *Paliurus ramosissimus* (Lour.) Poir. ethanol extract.

2. Preparation of *Paliurus ramosissimus* (Lour.) Poir. Methanol Extract

Take 1 kg of the whole plant of fresh *Paliurus ramosissimus* (Lour.) Poir., crush, add methanol of 6 times of the volume of *Paliurus ramosissimus* (Lour.) Poir., reflux to extract 3 times, collect the extract liquid, recover methanol under reduced pressure, and freeze-dry the concentrated to obtain *Paliurus ramosissimus* (Lour.) Poir. methanol extract.

3. Preparation of *Paliurus ramosissimus* (Lour.) Poir. Petroleum Ether Extract (1) Take *Paliurus ramosissimus* (Lour.) Poir. ethanol extract concentrate, extract with petroleum ether, recover petroleum ether, and dry.

(2) Take *Paliurus ramosissimus* (Lour.) Poir. methanol extract dried sample, suspend with 10 times of water, extract with petroleum ether, recover petroleum ether, and dry.

(3) Take *Paliurus ramosissimus* (Lour.) Poir. ethanol extract dried sample, reflux to extract with 10 times of petroleum ether, recover petroleum ether, and dry.

4. Preparation of *Paliurus ramosissimus* (Lour.) Poir. Ethyl Acetate Extract (1) Take *Paliurus ramosissimus* (Lour.) Poir. ethanol extract concentrate, extract with 10 times of petroleum ether and then with 10 times of ethyl acetate, recover ethyl acetate, and dry.

(2) Take *Paliurus ramosissimus* (Lour.) Poir. methanol extract dried sample, suspend with 10 times of water, extract with 10 times of petroleum ether and then with 10 times of ethyl acetate, recover ethyl acetate, and dry.

(3) Take *Paliurus ramosissimus* (Lour.) Poir. ethanol extract dried sample, reflux to extract with 6 times of ethyl acetate 2 times, recover ethyl acetate, and dry.

5. Preparation of *Paliurus ramosissimus* (Lour.) Poir. Ethyl Acetate Extract Tablets Take 300 g of *Paliurus ramosissimus* (Lour.) Poir. ethyl acetate extract, crush, pass through a 40-mesh sieve, add 100 g of microcrystalline cellulose, 57.5 g of lactose, 20 g of cross-linked sodium carboxymethyl cellulose, mix well, evenly spray appropriate amount of 95% (volume concentration) ethanol solution, granulate with wet extrusion, pass through a 24-mesh sieve, dry at 50° C., then add 20 g of cross-linked sodium carboxymethyl cellulose and 2.5 g of magnesium stearate, fully mix, compress to tablets to obtain *Paliurus ramosissimus* (Lour.) Poir. ethyl acetate extract tablets;

6. Preparation of *Paliurus ramosissimus* (Lour.) Poir. Ethanol Extract Granules Take 1000 g of *Paliurus ramosissimus* (Lour.) Poir. ethanol extract, crush, pass through a 40-mesh sieve, add 4000 g of sugar powder, mix well, evenly spray appropriate amount of 95% (volume concentration) ethanol solution, granulate with wet extrusion, pass through a 24-mesh sieve, dry at 50° C., and uniform granules to obtain *Paliurus ramosissimus* (Lour.) Poir. ethanol extract granules;

7. Preparation of *Paliurus ramosissimus* (Lour.) Poir. Methanol Extract Ointments Weigh 115 g of octadecanol, 115 g of white petrolatum and 70 g of glyceryl monostearate, heat to melt to obtain the oil phase, add 40 g of *Paliurus ramosissimus* (Lour.) Poir. methanol extract; weigh 100 g of glycerol, 15 g of sodium lauryl sulfate and 0.01 g of cysteine hydrochloride, add 650 ml of water to dissolve to obtain the aqueous phase; heat separately to 75° C.-80° C., slowly add the water phase into the oil phase with stirring, then continue stirring for 15 minutes to obtain *Paliurus ramosissimus* (Lour.) Poir. methanol extract ointments.

8. Preparation of *Paliurus ramosissimus* (Lour.) Poir. Ethanol Extract Gels

Take 10 g of carbomer, pour into 420 ml of purified water, stir to swell, add 100 ml of propylene glycol and stir to dissolve, add 18 g of triethanolamine dropwise with stirring to prepare the gel matrix; take 100 g of *Paliurus ramosissimus* (Lour.) Poir. ethanol extract and 2 g of ethylparaben, dissolve in 350 ml of ethanol, add the gel matrix with stirring, and stir well.

9. Preparation of *Paliurus ramosissimus* (Lour.) Poir. Ethanol Extract Plastics Take 40 g of polyvinyl alcohol 124, swell in 400 ml of purified water; take 100 g of *Paliurus ramosissimus* (Lour.) Poir. ethanol extract, dissolve in 400 ml of ethanol, then add 100 ml of glycerin, stir well, slowly add into polyvinyl alcohol solution, stir well, filter, and add ethanol over a filter to 1000 ml.

10. Preparation of *Paliurus ramosissimus* (Lour.) Poir. Petroleum Ether Extract Liniment Take 100 g of *Paliurus ramosissimus* (Lour.) Poir. petroleum ether extract powder, place in a mortar, add 500 ml of peanut oil, grind well, then slowly add saturated calcium hydroxide aqueous solution to 1000 ml, and grind to homogeneous white milky substance.

11. Preparation of *Paliurus ramosissimus* (Lour.) Poir. Ethanol Extract Lotions Take 100 g of *Paliurus ramosissimus* (Lour.) Poir. ethanol extract powder, place in a mortar, add 50 ml of glycerol and appropriate amount of purified water, grind into a paste, and gradually add purified water until mix completely.

(II) Study on Antifungal Activity of *Paliurus ramosissimus* (Lour.) Poir. Extract Weigh 1 g of *Paliurus ramosissimus* (Lour.) Poir. ethanol extract prepared in Embodiment 1 (1), dissolve with 5% isopropanol solution to 10 ml, filter through a 0.22 μm membrane for sterilization. Take 1 ml of sterilized solution, add into 9 ml PDA medium which is melt and cooled to about 50° C., shake well, quickly pour into a Petri dish with diameter of 6 cm and allow to stand to make PDA of the culture plate containing 10 mg/ml *Paliurus ramosissimus* (Lour.) Poir. extract. Use same volume of 5% isopropyl alcohol solution to make the blank control PDA culture plate.

Move bacterial inoculum which has been well cut, to the above drug-containing PDA culture plate, incubate at 25° C., when bacterial colonies in the control group are approaching the edge of the dish, determine colony diameter of all colonies on the culture plate with criss-cross method, and calculate fungus inhibition rate after correction.

The results are shown in Table 13. *Paliurus ramosissimus* (Lour.) Poir. alcohol extract inhibits various types of tested fungi significantly. Because tested fungi are common pathogenic fungi with significant representation, the results suggest that *Paliurus ramosissimus* (Lour.) Poir. alcohol extract has strong antifungal activity, which is expected to be applied to the preparation of antifungal drugs.

TABLE 13

Effect of *Paliurus ramosissimus* (Lour.) Poir. alcohol extract on inhibition of various fungi (n = 3, $\bar{x} \pm s$)

| Strains | Fungus inhibition rate (%) |
| --- | --- |
| *Candida albicans* | 87.53 ± 8.36 |
| *Trichophyton rubrum* | 80.46 ± 10.24 |
| *Trichophyton mentagrophytes* | 72.69 ± 11.53 |
| *Trichophyton violaceum* | 90.16 ± 14.36 |
| *Trichophyton tonsurans* | 54.39 ± 8.67 |
| *Trichophyton verrucosum* | 42.63 ± 12.81 |
| *Microsporum nanum* | 60.54 ± 10.33 |
| *Microsporum canis* | 61.32 ± 7.65 |
| *Sporothrix schenckii* | 76.87 ± 15.69 |
| *Phialophora compactum* | 66.63 ± 17.65 |
| *Exophiala dermatitidis* | 62.65 ± 8.87 |
| *Hormodendrum pedrosei* | 53.13 ± 10.08 |

V. *Paliurus ramosissimus* (Lour.) Poir. Leaf Extract in the Treatment of Immune Dysfunction or (and) Autoimmune Diseases (I) Preparation of *Paliurus ramosissimus* (Lour.) Poir. Extract 1. Preparation of Whole Plant Ethanol Extract Take 1 kg of *Paliurus ramosissimus* (Lour.) Poir. whole plant, add 95% ethanol of 8 times the weight, soak for one day, then crush, add 95% ethanol of 10 times the weight, soak for 2 days, collect the extract liquid, recover ethanol at 50° C. under reduced pressure until no ethanol smell and dry to obtain *Paliurus ramosissimus* (Lour.) Poir. ethanol extract.

2. Preparation of Stem and Leaf Ethanol, Petroleum Ether and Ethyl Acetate Extracts Take 1 kg of *Paliurus ramosissimus* (Lour.) Poir. stems and leaves, add 95% ethanol of 10 times the weight, soak for one day, then crush, add 95% ethanol of 10 times the weight for reflux extraction, collect the extract liquid, recover ethanol at 60° C. under reduced pressure until no ethanol smell and dry to obtain *Paliurus ramosissimus* (Lour.) Poir. ethanol extract. Disperse *Paliurus ramosissimus* (Lour.) Poir. ethanol extract in water, and extract with petroleum ether and ethyl acetate in sequence, to obtain petroleum ether extract and ethyl acetate extract.

3. Preparation of Whole Plant Petroleum Ether and Ethyl Acetate Extracts

Take 1 kg of *Paliurus ramosissimus* (Lour.) Poir. whole plant, add methanol of 10 times the weight, soak for one day, then crush, add methanol of 8 times the weight, soak for 2 days, collect the extract liquid, recover methanol at 40° C. under reduced pressure, and dry to obtain *Paliurus ramosissimus* (Lour.) Poir. methanol extract. Disperse *Paliurus ramosissimus* (Lour.) Poir. methanol extract in water, and extract with petroleum ether and ethyl acetate in sequence, to obtain petroleum ether extract and ethyl acetate extract.

4. Ingredient Quantitative Analysis

Take three portions of 0.1 g of *Paliurus ramosissimus* (Lour.) Poir. stem and leaf petroleum ether extract, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of *Paliurus ramosissimus* (Lour.) Poir extract contains 23 g of triterpenoids.

Take three portions of 0.1 g of *Paliurus ramosissimus* (Lour.) Poir. stem and leaf petroleum ether extract, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance at wavelength of 510 nm, and calculate total flavonoids content in sample test solution (flavonoids as rutin). The calculation has showed that 1 g of *Paliurus ramosissimus* (Lour.) Poir. extract contains 103 mg of flavonoids.

Take three portions of 0.1 g of *Paliurus ramosissimus* (Lour.) Poir. stem and leaf petroleum ether extract, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer). Titrate with 1 mmol·L−1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of *Paliurus ramosissimus* (Lour.) Poir. extract contains 21 g of alkaloids.

Take three portions of 0.1 g of *Paliurus ramosissimus* (Lour.) Poir. stem and leaf petroleum ether extract, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add 70% ethanol to the mark, and shake well. Precisely pipette 3 ml, and transfer to 25-ml volumetric flasks, determine absorbance at wavelength of 340 nm, and Calculate total coumarins content in sample test solution (coumarins as umbelliferone). The calculation has showed that 1 g of *Paliurus ramosissimus* (Lour.) Poir. extract contains 10.2 mg of coumarins.

Take three portions of 0.1 g of *Paliurus ramosissimus* (Lour.) Poir. stem and leaf ethyl acetate extract, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of *Paliurus ramosissimus* (Lour.) Poir extract contains 108 mg of triterpenoids.

Take three portions of 0.1 g of *Paliurus ramosissimus* (Lour.) Poir. stem and leaf ethyl acetate extract, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance at wavelength of 510 nm, and calculate total flavonoids content in sample test solution (flavonoids as rutin). The calculation has showed that 1 g of *Paliurus ramosissimus* (Lour.) Poir. extract contains 497 mg of flavonoids.

Take three portions of 0.1 g of *Paliurus ramosissimus* (Lour.) Poir. whole plant ethyl acetate extract, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer). Titrate with 1 mmol·L−1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of *Paliurus ramosissimus* (Lour.) Poir. extract contains 107 mg of alkaloids.

Take three portions of 0.1 g of *Paliurus ramosissimus* (Lour.) Poir. whole plant ethyl acetate extract, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add 70% ethanol to the mark, and shake well. Precisely pipette 3 ml, and transfer to 25-ml volumetric flasks, determine absorbance at wavelength of 340 nm, and Calculate total coumarins content in sample test solution (coumarins as umbelliferone). The calculation has showed that 1 g of *Paliurus ramosissimus* (Lour.) Poir. extract contains 186 mg of coumarins.

(II) Preparation of *Paliurus ramosissimus* (Lour.) Poir. Preparations

1. Preparation of Tablets

Take 300 g of *Paliurus ramosissimus* (Lour.) Poir. whole plant ethanol extract, add suitable excipient, such as: 100 g of microcrystalline cellulose, 57.5 g of lactose, 20 g of cross-linked sodium carboxymethyl cellulose, etc., and compress into tablets.

2. Preparation of Capsules

Take *Paliurus ramosissimus* (Lour.) Poir. stem and leaf ethyl acetate extract, add suitable excipient, such as: lactose, compressible starch, carboxymethyl starch, microcrystalline cellulose, etc., to make capsules.

3. Preparation of Granules

Take *Paliurus ramosissimus* (Lour.) Poir. whole plant methanol extract, add suitable excipient, such as: lactose, starch, methyl cellulose, hydroxymethyl cellulose, hydroxypropylmethyl cellulose, hydroxypropyl cellulose, polyvinylpyrrolidone, silica powder etc., to make granules.

4. Preparation of Ointments

Take *Paliurus ramosissimus* (Lour.) Poir. stem and leaf petroleum ether extract, add suitable excipient, such as: octadecanol, glycerol monostearate, glycerin, stearic acid etc., to make ointments.

5. Preparation of Suppositories

Take *Paliurus ramosissimus* (Lour.) Poir. whole plant ethanol extract, add suitable excipient, such as: mixed fatty acid glycerides, PEG, beeswax etc., to make suppositories.

(III) In Vitro Cytological Studies

1. Effect of *Paliurus ramosissimus* (Lour.) Poir. Extract on Spleen Lymphocyte in Vitro Proliferation in Mice 1.1 Preparation of Mouse Spleen Lymphocytes Take spleen of Kunming mice in a sterile manner, place in a dish filled with appropriate amount of RPMI1640 culture medium, remove the connective tissue, grind with a syringe needle, filter through a 200 mesh screen, transfer to a centrifuge tube, wash with RPMI1640, collect cells, and add 1 ml of erythrocyte lysate. After standing at 4° C. for 5-10 min, centrifuge at 1500 r/min for 5 min, discard the supernatant, wash twice with RPMI1640 medium, and finally suspend the cells in 1 ml RPMI1640 complete medium. Determine survival rate by trypan blue, and the results have showed that the spleen cell survival rate is greater than 95%. Appropriately dilute the above spleen cell suspension, and adjust cell density to $2\times10^6$ cells/ml for future use.

1.2. Effect of *Paliurus ramosissimus* (Lour.) Poir. Extract on Spleen Lymphocyte in Vitro Proliferation in Mice On a 96-well plate, to each well, add 100 μl of spleen cell suspension of $2\times10^6$ cells/ml. Set blank group, control group and *Paliurus ramosissimus* (Lour.) Poir. extract groups. For the control group, to each well, add 100 μl of RPMI1640 complete medium; for *Paliurus ramosissimus* (Lour.) Poir. extract group, to each well, add 100 μl of RPMI1640 complete medium solution containing various concentration of *Paliurus ramosissimus* (Lour.) Poir. extract; and the blank group contains medium only. Place the 96-well plate in 37° C., 5% $CO_2$ incubator for 60 h. Take out the plate, draw the liquids in wells, wash three times with PBS, add 100 μl of culture medium and 20 μl of MTT buffer (5 mg·ml$^{-1}$), and place in 37° C., 5% $CO_2$ incubator for 4 h. Take out the plate, carefully draw the supernatant, add 150 μl of dimethylsulfoxide, place the plate on a microplate shaker, shake for 10 min so that the formed formazan particles are fully dissolved, and determine absorbance with microplate reader at wavelength of 490 nm. Record the results and calculate the average in vitro survival rate of mouse spleen cells by *Paliurus ramosissimus* (Lour.) Poir. extract, according to formula (1).

$$\text{Average in vitro survival rate (\%)} = \frac{\text{Experiment group A value-Blank group A value}}{\text{Control group A value-Blank group A value}} \times 100\% \quad (1)$$

The results have showed that, when the concentration of *Paliurus ramosissimus* (Lour.) Poir. extract is 0.004 mg/ml, 0.02 mg/ml, and 0.2 mg/ml, the average survival rate of mouse spleen cells is 117.85%, 107.21% and 77.46%. The results have indicated that low concentration *Paliurus ramosissimus* (Lour.) Poir. extract can promote the proliferation of mouse spleen cells in vitro, while high concentration *Paliurus ramosissimus* (Lour.) Poir. extract inhibits the proliferation of spleen cells.

2. Effect of *Paliurus ramosissimus* (Lour.) Poir. Extract on ConA-Induced In Vitro Proliferation of Splenocytes On a 96-well plate, to each well, add 100 μl of spleen cell suspension of $2 \times 10^6$ cells/ml. Set blank group, control group, ConA group and *Paliurus ramosissimus* (Lour.) Poir. extract groups. For the control group, to each well, add 100 μl of RPMI1640 complete medium; For the ConA group, to each well, add 100 μl of RPMI1640 complete medium solution containing 25 μg/ml ConA; for *Paliurus ramosissimus* (Lour.) Poir. extract group, to each well, add 100 μl of RPMI1640 complete medium solution containing various concentration of *Paliurus ramosissimus* (Lour.) Poir. extract (the solution also contains 25 μg/ml ConA); and the blank group contains medium only. Place the 96-well plate in 37° C., 5% $CO_2$ incubator for 60 h. Take out the plate, draw the liquids in wells, wash three times with PBS, add 100 μl of culture medium and 20 μl of MTT buffer (5 mg·ml$^{-1}$), and place in 37° C., 5% $CO_2$ incubator for 4 h. Take out the plate, carefully draw the supernatant, add 150 μl of dimethylsulfoxide, place the plate on a microplate shaker, shake for 10 min so that the formed formazan particles are fully dissolved, and determine absorbance with microplate reader at wavelength of 490 nm. Record the results and calculate the average in vitro survival rate of mouse spleen cells by ConA group and *Paliurus ramosissimus* (Lour.) Poir. Extract group, according to formula (1); Calculate proliferation rate of ConA-induced in vitro proliferation of splenocytes by *Paliurus ramosissimus* (Lour.) Poir. extract, according to formula (2).

$$\text{Relative proliferation rate (\%)} = \frac{(\text{Experimental group} - 1)}{\text{ConA Control group}} \times 100\% \quad (2)$$

The results have showed that, when the concentration of *Paliurus ramosissimus* (Lour.) Poir. extract is 0.004 mg/ml, 0.02 mg/ml, and 0.2 mg/ml, the relative proliferation rate to ConA group is 15.11%, 5.69% and −14.35%, indicating that low concentration *Paliurus ramosissimus* (Lour.) Poir. extract can promote the ConA-induced in vitro proliferation of splenocytes, while high concentration *Paliurus ramosissimus* (Lour.) Poir. extract inhibits the proliferation.

3. Effect of *Paliurus ramosissimus* (Lour.) Poir. Extract on LPS-Induced In Vitro Proliferation of Splenocytes On a 96-well plate, to each well, add 100 μl of spleen cell suspension of $2 \times 10^6$ cells/ml. Set blank group, control group, LPS group and *Paliurus ramosissimus* (Lour.) Poir. extract groups. For the control group, to each well, add 100 μl of RPMI1640 complete medium; For the LPS group, to each well, add 100 μl of RPMI1640 complete medium solution containing 20 μg/ml LPS; for *Paliurus ramosissimus* (Lour.) Poir. extract group, to each well, add 100 μl of RPMI1640 complete medium solution containing various concentration of *Paliurus ramosissimus* (Lour.) Poir. extract (the solution also contains 20 μg/ml LPS); and the blank group contains medium only. Place the 96-well plate in 37° C., 5% $CO_2$ incubator for 60 h. Take out the plate, draw the liquids in wells, wash three times with PBS, add 100 μl of culture medium and 20 μl of MTT buffer (5 mg·ml$^{-1}$), and place in 37° C., 5% $CO_2$ incubator for 4 h. Take out the plate, carefully draw the supernatant, add 150 μl of dimethylsulfoxide, place the plate on a microplate shaker, shake for 10 min so that the formed formazan particles are fully dissolved, and determine absorbance with microplate reader at wavelength of 490 nm. Record the results and calculate the average in vitro survival rate of mouse spleen cells by LPS group and *Paliurus ramosissimus* (Lour.) Poir. Extract group, according to formula (1); Calculate proliferation rate of LPS-induced in vitro proliferation of splenocytes by *Paliurus ramosissimus* (Lour.) Poir. extract, according to formula (2).

The results have showed that, when the concentration of *Paliurus ramosissimus* (Lour.) Poir. extract is 0.004 mg/ml, 0.02 mg/ml, and 0.2 mg/ml, the relative proliferation rate to LPS group is 34.37%, 20.48% and −15.60%, indicating that low concentration *Paliurus ramosissimus* (Lour.) Poir. extract can promote the LPS-induced in vitro proliferation of splenocytes, while high concentration *Paliurus ramosissimus* (Lour.) Poir. extract inhibits the proliferation, which is consistent with the conclusion drawn from the above study of ConA-induced in vitro proliferation of splenocytes that *Paliurus ramosissimus* (Lour.) Poir. extract has bi-directional immunomodulatory effect.

(IV) Pharmacological Verification

1. Effect of Ethanol, Methanol, Petroleum Ether Extracts and Ethyl Acetate Extract on Nonspecific Immune Function of Immunocompromised Mice (Peritoneal Macrophages Method)

Take 80 KM mice, randomly divide into 8 groups with stratification of body weight, namely suspension control group (0.5% mucilage tragacanth), model control group (0.5% mucilage tragacanth), positive control group (*coriolus versicolor* polysaccharide), ethyl acetate extract low-dose group, ethyl acetate extract high-dose group, ethanol extract group, methanol extract group, and petroleum ether extract group. In all groups, mice receive test substance or suspension via intragastric administration once a day for 14 consecutive days. Except suspension control group, mice in other groups receive intraperitoneal injection of 25 mg/kg cyclophosphamide in normal saline solution at day 8, 10 and 12 to introduce immunosuppression. At day 13 and 14, apply intraperitoneal injection of 6% starch solution respectively. 1 h after the last administration at day 14, apply intraperitoneal injection of 1 ml of 5% chicken erythrocytes in saline suspension; 30 min later, sacrifice the mice by cervical dislocation, apply intraperitoneal injection of 2 ml saline, and gently massage the abdomen. 1 min later, cut open abdomen, draw 1 ml of peritoneal washings, evenly drop on two slides, place in a wet box, and incubate at 37° C. for 30 min. Rinse in saline, dry, fix with 1:1 acetone-methanol solution, stain with 4% (v/v) Giemsa-PBS for 3 min, rinse with distilled water and dry, perform microscopic examination, and calculate the percentage of phagocytosis.

TABLE 14

Effect of *Paliurus ramosissimus* (Lour.) Poir. extracts on peritoneal macrophage phagocytosis of immunocompromised mice (n = 10, $\bar{x} \pm s$)

| Group | Dose | Percentage of phagocytosis |
|---|---|---|
| Suspension control | — | 0.40 ± 0.09** |
| Model control | — | 0.17 ± 0.07 |
| Positive control (*coriolus versicolor* polysaccharide) | 0.4 g/kg | 0.36 ± 0.11** |
| Ethyl acetate extract low-dose | 0.1 g/kg | 0.26 ± 0.08** |
| Ethyl acetate extract high-dose | 0.4 g/kg | 0.32 ± 0.10** |
| Methanol extract | 1.2 g/kg | 0.32 ± 0.11** |

TABLE 14-continued

Effect of *Paliurus ramosissimus* (Lour.) Poir. extracts on peritoneal macrophage phagocytosis of immunocompromised mice (n = 10, x̄ ± s)

| Group | Dose | Percentage of phagocytosis |
|---|---|---|
| Petroleum ether extract | 1.2 g/kg | 0.31 ± 0.07** |
| Ethanol extract | 1.2 g/kg | 0.36 ± 0.11** |

Compared with the model control group, *P < 0.05, **P < 0.01

The results are shown in Table 14. Intragastric administration of *Paliurus ramosissimus* (Lour.) Poir. ethyl acetate extract of 0.1 g/kg and above for 14 days can significantly improve the phagocytic activity of peritoneal macrophages of immunocompromised mice, and the strength of 0.4 g/kg dose group does not show significant difference with that of *coriolus versicolor* polysaccharide group; 1.2 g/kg of ethanol, methanol, petroleum ether extracts can effectively enhance phagocytic activity of peritoneal macrophages of immunocompromised mice, suggesting that the four extracts have good immune enhancement activity.

2. Effect of ethanol, methanol, petroleum ether extracts and ethyl acetate extract on specific immune function of immunocompromised mice (2,4-difluorophenyl nitrate-induced ear edema method).

Take 80 KM mice, randomly divide into 8 groups with stratification of body weight, namely suspension control group (0.5% mucilage tragacanth), model control group (0.5% mucilage tragacanth), positive control group (*coriolus versicolor* polysaccharide), ethyl acetate extract low-dose group, ethyl acetate extract high-dose group, ethanol extract group, methanol extract group, and petroleum ether extract group. In all groups, mice receive test substance or suspension via intragastric administration once a day for 14 consecutive days. Except suspension control group, mice in other groups receive intraperitoneal injection of 25 mg/kg cyclophosphamide in normal saline solution at day 8, 10 and 12 to introduce immunosuppression. At day 9 of administration, smear 25 μl of 1% 2,4-difluorophenyl nitrate (DNFB) solution (take 100 mg of DNFB, add to the 1:1 acetone-vegetable oil mixture, mix well, and volume to 10 ml) on the abdomen of mice; 1 h after the administration at day 13, smear 10 μl of 1% DNFB solution on the left ear of mice; 24 hours of the smear, i.e., 1 hour after last administration, sacrifice the mice by cervical dislocation, weigh the ear and calculate the degree of ear edema.

TABLE 15

Effect of *Paliurus ramosissimus* (Lour.) Poir. extract on ear edema induced by DNFB of immunocompromised mice (n = 10, x̄ ± s)

| Group | Dose | Ear edema (mg) |
|---|---|---|
| Suspension control | — | 11.05 ± 1.72** |
| Model control | — | 6.06 ± 0.63 |
| Positive control (*coriolus versicolor* polysaccharide) | 0.4 g/kg | 7.11 ± 1.73** |
| Ethyl acetate extract low-dose | 0.1 g/kg | 7.20 ± 1.32* |
| Ethyl acetate extract high-dose | 0.4 g/kg | 8.04 ± 1.55** |
| Methanol extract | 1.2 g/kg | 8.31 ± 1.45** |
| Petroleum ether extract | 1.2 g/kg | 7.31 ± 1.56* |
| Ethanol extract | 1.2 g/kg | 7.09 ± 1.06* |

Compared with the model control group, *P < 0.05, **P < 0.01

The results are shown in Table 15. *Paliurus ramosissimus* (Lour.) Poir. ethyl acetate extract can improve ear edema induced by DNFB of immunocompromised mice, suggesting that it has activity of enhancing cellular immune function for immunocompromised animals; the effect of 1.2 g/kg of ethanol, methanol, petroleum ether extracts is similar to that of ethyl acetate extract, suggesting that the four extracts have good enhancing effect on specific immune of immunocompromised animals.

3. Effect of Ethanol, Methanol, Petroleum Ether Extracts and Ethyl Acetate Extract on Nonspecific Immune Function of Normal Mice (Peritoneal Macrophages Method)

Take 80 KM mice, randomly divide into 8 groups with stratification of body weight, namely suspension control group (0.5% mucilage tragacanth), enhancement effect positive control group (*coriolus versicolor* polysaccharide), Inhibition effect positive control group (Cyclophosphamide), ethyl acetate extract low-dose group, ethyl acetate extract high-dose group, ethanol extract group, methanol extract group, and petroleum ether extract group. Except that the mice in inhibition effect positive control group receive one dose of subcutaneous injection at day 13, mice in other groups receive test substance or suspension via intragastric administration once a day for 14 consecutive days. At day 13 and 14, apply intraperitoneal injection of 6% starch solution respectively. 1 h after the last administration at day 14, apply intraperitoneal injection of 1 ml of 5% chicken erythrocytes in saline suspension; 30 min later, sacrifice the mice by cervical dislocation, apply intraperitoneal injection of 2 ml saline, and gently massage the abdomen. 1 min later, cut open abdomen, draw 1 ml of peritoneal washings, evenly drop on two slides, place in a wet box, and incubate at 37° C. for 30 min. Rinse in saline, dry, fix with 1:1 acetone-methanol solution, stain with 4% (v/v) Giemsa-PBS for 3 min, rinse with distilled water and dry, perform microscopic examination, and calculate the percentage of phagocytosis.

TABLE 16

Effect of *Paliurus ramosissimus* (Lour.) Poir. extracts on peritoneal macrophage phagocytosis of normal mice (n = 10, x̄ ± s)

| Group | Dose | Percentage of phagocytosis |
|---|---|---|
| Blank control | — | 0.49 ± 0.11 |
| Enhancement effect positive control (*Coriolus versciclor* polysaccharides) | 0.4 g/kg | 0.47 ± 0.19 |
| Inhibition effect positive control (Cyclophosphamide) | 0.1 g/kg | 0.12 ± 0.03** |
| Ethyl acetate extract low-dose | 0.1 g/kg | 0.41 ± 0.13 |
| Ethyl acetate extract high-dose | 0.4 g/kg | 0.37 ± 0.08* |
| Methanol extract | 1.2 g/kg | 0.33 ± 0.07** |
| Petroleum ether extract | 1.2 g/kg | 0.36 ± 0.12* |
| Ethanol extract | 1.2 g/kg | 0.36 ± 0.10** |

Compared with the suspension control group, *P < 0.05, **P < 0.01

The results are shown in Table 16. Intragastric administration of *Paliurus ramosissimus* (Lour.) Poir. ethyl acetate extract of 0.4 g/kg for 14 days can improve the phagocytic activity of peritoneal macrophages of normal mice, while dose of 0.1 g/kg dose group does not show obvious effect; 1.2 g/kg of ethanol, methanol, petroleum ether extracts show inhibitory effect of varying degrees, suggesting that the four extracts have mild immune inhibitory effect on normal animals.

4. Effect of Ethanol, Methanol, Petroleum Ether Extracts and Ethyl Acetate Extract on Specific Immune Function of Normal Mice (2,4-Difluorophenyl Nitrate-Induced Ear Edema Method)

Take 80 KM mice, randomly divide into 8 groups with stratification of body weight, namely suspension control group (0.5% mucilage tragacanth), enhancement effect positive control group (*coriolus versicolor* polysaccharide), Inhibition effect positive control group (Cyclophosphamide), ethyl acetate extract low-dose group, ethyl acetate extract high-dose group, ethanol extract group, methanol extract group, and petroleum ether extract group. Except that the mice in inhibition effect positive control group receive one dose of subcutaneous injection at day 13, mice in other groups receive test substance or suspension via intragastric administration once a day for 14 consecutive days. At day 9 of administration, smear 25 µl of 1% 2,4-difluorophenyl nitrate (DNFB) solution (take 100 mg of DNFB, add to the 1:1 acetone-vegetable oil mixture, mix well, and volume to 10 ml) on the abdomen of mice; 1 h after the administration at day 13, smear 10 µl of 1% DNFB solution on the left ear of mice; 24 hours of the smear, i.e., 1 hour after last administration, sacrifice the mice by cervical dislocation, weigh the ear and calculate the degree of ear edema.

TABLE 17

Effect of *Paliurus ramosissimus* (Lour.) Poir. extract on ear edema induced by DNFB of normal mice (n = 10, $\bar{x} \pm s$)

| Group | Dose | Ear edema (mg) |
| --- | --- | --- |
| Suspension control | — | 10.78 ± 1.19 |
| Model control | 0.4 g/kg | 10.59 ± 1.33 |
| Positive control (*coriolus versicolor* polysaccharide) | 0.1 g/kg | 5.66 ± 0.72** |
| Ethyl acetate extract low-dose | 0.1 g/kg | 9.54 ± 1.21* |
| Ethyl acetate extract high-dose | 0.4 g/kg | 7.28 ± 0.98** |
| Methanol extract | 1.2 g/kg | 7.15 ± 1.17** |
| Petroleum ether extract | 1.2 g/kg | 9.12 ± 1.34** |
| Ethanol extract | 1.2 g/kg | 8.52 ± 1.63** |

Compared with the suspension control group, *P < 0.05, **P < 0.01

The results are shown in Table 17. 0.1 g/kg of *Paliurus ramosissimus* (Lour.) Poir. ethyl acetate extract can inhibit ear edema induced by DNFB of normal mice, suggesting that it has certain inhibitory effect of cellular immune function on normal animals; the effect of 1.2 g/kg of ethanol, methanol, petroleum ether extracts is similar to that of ethyl acetate extract, suggesting that the four extracts have certain specific immune inhibitory effect.

5. The Therapeutic Effect on Mice Experimental Lupus and Effect on Cellular Immunity of Ethanol, Methanol, Petroleum Ether Extracts and Ethyl Acetate Extract Take 80 KM mice, randomly divide into 8 groups with stratification of body weight, namely suspension control group (0.5% mucilage tragacanth), model control group (0.5% mucilage tragacanth), positive control group (tripterygium glycosides), ethyl acetate extract low-dose group, ethyl acetate extract high-dose group, ethanol extract group, methanol extract group, and petroleum ether extract group. Except the suspension control group, mice in other groups receive intraperitoneal injection of 0.5 ml/body pristine, and test substance or suspension via intragastric administration once a day for 30 consecutive days. 24 h after last administration, draw 20 µl of orbital blood, centrifuge at 4° C. to separate the serum, and determine nti-dsDNA antibody level in serum by ELISA.

Take another group of animals, group in the same way and replicate the model. Day 24 after the injection of pristane, except the suspension control group, mice in other groups receive intraperitoneal injection of 0.2 ml/body 5% chicken erythrocytes in saline suspension, continue the drug administration until day 30 after the injection of pristine. 24 h after last administration, draw 20 µl of orbital blood, add 1 ml of saline, then 0.5 ml of 4% chicken erythrocytes in saline suspension and 0.5 ml of 10% guinea pig serum respectively, after mixing, incubate at 37° C. for 0.5 h, centrifuge at 3000 rpm for 10 min, draw 1 ml of the supernatant, add 3 ml of Drabkin's reagent, and perform colorimetry at 540 nm.

TABLE 18

Effect of *Paliurus ramosissimus* (Lour.) Poir. extract on experimental lupus in mice (n = 10, $\bar{x} \pm s$)

| Group | Dose | Serum dsdna content (OD) | Hemolysin (OD × $10^{-1}$) |
| --- | --- | --- | --- |
| Suspension control | — | 0.26 ± 0.028** | 1.70 ± 0.19** |
| Model control | 0.4 g/kg | 2.56 ± 0.381 | 2.52 ± 0.29 |
| Positive control (Tripterygium glycosides) | 0.03 g/kg | 1.63 ± 0.101** | 0.82 ± 0.17** |
| Ethyl acetate extract low-dose | 0.1 g/kg | 2.23 ± 0.285 | 2.09 ± 0.31* |
| Ethyl acetate extract high-dose | 0.4 g/kg | 2.08 ± 0.452* | 1.82 ± 0.26** |
| Methanol extract | 1.2 g/kg | 2.25 ± 0.309 | 2.00 ± 0.24** |
| Petroleum ether extract | 1.2 g/kg | 2.10 ± 0.347* | 2.12 ± 0.25* |
| Ethanol extract | 1.2 g/kg | 2.11 ± 0.251* | 2.04 ± 0.30** |

Compared with the model control group, *P < 0.05, **P < 0.01

The results are shown in Table 18. 0.4 g/kg of *Paliurus ramosissimus* (Lour.) Poir. ethyl acetate extract can effectively reduce dsDNA antibody level in serum of mice with experimental lupus, suggesting that it may be used to treat lupus; the effect of 1.2 g/kg of ethanol, methanol, and petroleum ether extracts is similar to that of ethyl acetate extract, suggesting that the four extracts have some effects on lupus. Lupus may manifest as abnormally elevated humoral immunity, and in the study, hemolysin level in model animals is significantly higher than that in normal animals, and 0.1 g/kg of *Paliurus ramosissimus* (Lour.) Poir. ethyl acetate extract can effectively reduce such abnormally elevated hemolysin level, and 1.2 g/kg of ethanol, methanol, and petroleum ether extracts are similar to that of ethyl acetate extract, suggesting that the four extracts have significant inhibitory effect on abnormal immune hyperthyroidism.

VI. The Treatment of Oral and Gastrointestinal Inflammation and Ulcer by *Paliurus Ramosissimus* (Lour.) Poir. Extract (I) Preparation of *Paliurus ramosissimus* (Lour.) Poir. Extract 1. Preparation of Whole Plant Ethanol Extract Take 1 kg of *Paliurus ramosissimus* (Lour.) Poir. whole plant, add 95% ethanol of 8 times the weight, soak for one day, then crush, add 95% ethanol of 10 times the weight, soak for 2 days, collect the extract liquid, recover ethanol at 50° C. under reduced pressure until no ethanol smell and dry to obtain *Paliurus ramosissimus* (Lour.) Poir. ethanol extract.

2. Preparation of Stem and Leaf Ethanol, Petroleum Ether and Ethyl Acetate Extracts Take 1 kg of *Paliurus ramosissimus* (Lour.) Poir. stems and leaves, add 95% ethanol of 10 times the weight, soak for one day, then crush, add 95% ethanol of 10 times the weight for reflux extraction, collect the extract liquid, recover ethanol at 60° C. under reduced pressure until no ethanol smell and dry to obtain *Paliurus ramosissimus* (Lour.) Poir. ethanol extract. Disperse *Paliurus ramosissimus* (Lour.) Poir. ethanol extract in water, and extract with petroleum ether and ethyl acetate in sequence, to obtain petroleum ether extract and ethyl acetate extract.

3. Preparation of Whole Plant Petroleum Ether and Ethyl Acetate Extracts

Take 1 kg of *Paliurus ramosissimus* (Lour.) Poir. whole plant, add methanol of 10 times the weight, soak for one day, then crush, add methanol of 8 times the weight, soak for 2 days, collect the extract liquid, recover methanol at 40° C. under reduced pressure, and dry to obtain *Paliurus ramosissimus* (Lour.) Poir. methanol extract. Disperse *Paliurus ramosissimus* (Lour.) Poir. methanol extract in water, and extract with petroleum ether and ethyl acetate in sequence, to obtain petroleum ether extract and ethyl acetate extract.

4. Ingredient Quantitative Analysis

Take three portions of 0.1 g of *Paliurus ramosissimus* (Lour.) Poir. stem and leaf petroleum ether extract, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of *Paliurus ramosissimus* (Lour.) Poir extract contains 23 g of triterpenoids.

Take three portions of 0.1 g of *Paliurus ramosissimus* (Lour.) Poir. stem and leaf petroleum ether extract, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance at wavelength of 510 nm, and calculate total flavonoids content in sample test solution (flavonoids as rutin). The calculation has showed that 1 g of *Paliurus ramosissimus* (Lour.) Poir. extract contains 103 mg of flavonoids.

Take three portions of 0.1 g of *Paliurus ramosissimus* (Lour.) Poir. stem and leaf petroleum ether extract, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer). Titrate with 1 mmol·L−1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of *Paliurus ramosissimus* (Lour.) Poir. extract contains 21 g of alkaloids.

Take three portions of 0.1 g of *Paliurus ramosissimus* (Lour.) Poir. stem and leaf petroleum ether extract, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add 70% ethanol to the mark, and shake well. Precisely pipette 3 ml, and transfer to 25-ml volumetric flasks, determine absorbance at wavelength of 340 nm, and Calculate total coumarins content in sample test solution (coumarins as umbelliferone). The calculation has showed that 1 g of *Paliurus ramosissimus* (Lour.) Poir. extract contains 10.2 mg of coumarins.

Take three portions of 0.1 g of *Paliurus ramosissimus* (Lour.) Poir. stem and leaf ethyl acetate extract, place in 10-ml volumetric flasks, add ethyl acetate to the mark, then precisely pipette 4 ml, and transfer to 10-ml volumetric flasks. After evaporating the solvent, add 0.4 ml of 5% vanillin-glacial acetic acid, 1.6 ml of perchloric acid, mix well, dilute with ethyl acetate to the mark, place in a 70° C. water bath for 15 min, cool to room temperature, transfer to 10-ml volumetric flasks, add ethyl acetate to the mark, shake well, determine absorbance at wavelength of 540 nm, and calculate total triterpenoids content in sample test solution (triterpenoids as ceanothic acid). The calculation has showed that 1 g of *Paliurus ramosissimus* (Lour.) Poir extract contains 108 g of triterpenoids.

Take three portions of 0.1 g of *Paliurus ramosissimus* (Lour.) Poir. stem and leaf ethyl acetate extract, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add water to the mark, and shake well. Precisely pipette 3 ml, and transfer to 25-ml volumetric flasks, determine absorbance at wavelength of 510 nm, and calculate total flavonoids content in sample test solution (flavonoids as rutin). The calculation has showed that 1 g of *Paliurus ramosissimus* (Lour.) Poir. extract contains 497 mg of total flavonoids.

Take three portions of 0.1 g of *Paliurus ramosissimus* (Lour.) Poir. whole plant ethyl acetate extract, precisely weigh, place in stoppered Erlenmeyer flasks, soak in 2 ml of 18% ammonia for 1 hour, add 30 ml of mixed solvent of ether 2-chloroform 2-ethanol (25:8:2.5), extract with ultrasound for 20 min, and pour the supernatant to a small conical flask, then add 30 ml of the above mixed solvent, cold soak for half an hour, then extract with ultrasound for 20 min, filter, wash the residues and filter paper with 15 ml of the same solvent in three times, combine the filtrates in a conical flask, evaporate in a 60° C. water bath, accurately add 10 ml of chloroform for complete dissolution, accurately pipette 5 ml, transfer to a small separating funnel, and add 6 ml of chloroform and 2 ml of buffer (pH=5.0, 0.2 M potassium hydrogen phthalate buffer). Titrate with 1 mmol·L−1 bromothymol blue solution, and continue shaking; when approaching the end, separate chloroform layer, add 5 ml of fresh chloroform, continue titration and shaking, allow to stand and separate layers, until the water layer appears slight yellow. Calculate total alkaloids content in sample test solution (alkaloids as paliurine B). The calculation has showed that 1 g of *Paliurus ramosissimus* (Lour.) Poir. extract contains 107 mg of alkaloids.

Take three portions of 0.1 g of *Paliurus ramosissimus* (Lour.) Poir. whole plant ethyl acetate extract, precisely weigh, place in 50-ml volumetric flasks, add appropriate amount of ethanol, dissolve with ultrasound, cool, add ethanol to the mark, and shake well. Precisely pipette 1 ml, and transfer to 10-ml volumetric flasks, add 70% ethanol to the mark, and shake well. Precisely pipette 3 ml, and transfer to 25-ml volumetric flasks, determine absorbance at wavelength of 340 nm, and Calculate total coumarins content in sample test solution (coumarins as umbelliferone). The calculation has showed that 1 g of *Paliurus ramosissimus* (Lour.) Poir. extract contains 186 mg of coumarins.

(II) Preparation of *Paliurus ramosissimus* (Lour.) Poir. Preparations

1. Preparation of Tablets

Take 300 g of *Paliurus ramosissimus* (Lour.) Poir. whole plant ethanol extract, add suitable excipient, such as: 100 g of microcrystalline cellulose, 57.5 g of lactose, 20 g of cross-linked sodium carboxymethyl cellulose, etc., and compress into tablets.

2. Preparation of Capsules

Take *Paliurus ramosissimus* (Lour.) Poir. stem and leaf ethyl acetate extract, add suitable excipient, such as: lactose, compressible starch, carboxymethyl starch, microcrystalline cellulose, etc., to make capsules.

3. Preparation of Granules

Take *Paliurus ramosissimus* (Lour.) Poir. whole plant methanol extract, add suitable excipient, such as: lactose, starch, methyl cellulose, hydroxymethyl cellulose, hydroxypropylmethyl cellulose, hydroxypropyl cellulose, polyvinylpyrrolidone, silica powder etc., to make granules.

4. Preparation of Ointments

Take *Paliurus ramosissimus* (Lour.) Poir. stem and leaf petroleum ether extract, add suitable excipient, such as: octadecanol, glycerol monostearate, glycerin, stearic acid etc., to make ointments.

5. Preparation of Suppositories

Take *Paliurus ramosissimus* (Lour.) Poir. whole plant ethanol extract, add suitable excipient, such as: mixed fatty acid glycerides, PEG, beeswax etc., to make suppositories.

(III) Pharmacology Verification of Uses of *Paliurus ramosissimus* (Lour.) Poir. Extract 1. Effect of Ethanol, Methanol, Petroleum Ether Extracts and Ethyl Acetate Extract on Pylorus Ligation Induced Experimental Gastric Ulcer in Rats.

Take 80 SD mice, randomly divide into 8 groups with stratification of body weight, namely model control group (0.5% mucilage tragacanth), positive control group (ranitidine), ethyl acetate extract low-dose group, ethyl acetate extract middle-dose group, ethyl acetate extract high-dose group, ethanol extract group, methanol extract group, and petroleum ether extract group. In all groups, mice receive test substance via intragastric administration once a day for 3 consecutive days. 1 h after the last administration, perform pylorus ligation, 15 hours after the surgery, sacrifice the animals by cervical dislocation, take out the stomach, fix with 1% formaldehyde for 20 min, then dissect, observe the extent of mucosal damage by stereoscopic microscope, and calculate ulcer index and ulcer inhibition rate.

TABLE 19

Effect of *Paliurus ramosissimus* (Lour.) Poir. extracts on pylorus ligation induced experimental gastric ulcer in rats (n = 10, $\bar{x} \pm s$)

| Group | Dose | Ulcer index | Inhibition rate (%) |
|---|---|---|---|
| Model control | — | 4.7 ± 1.7 | — |
| Positive control (ranitidine) | 60 mg/kg | 1.5 ± 0.4** | 68.1 |
| Ethyl acetate extract low-dose | 0.1 g/kg | 3.7 ± 1.4 | 21.3 |
| Ethyl acetate extract middle dose | 0.2 g/kg | 2.8 ± 0.7* | 40.4 |
| Ethyl acetate extract high-dose | 0.4 g/kg | 2.0 ± 1.0** | 57.4 |
| Methanol extract | 1.2 g/kg | 1.9 ± 0.6** | 59.6 |
| Petroleum ether extract | 1.2 g/kg | 2.0 ± 0.6** | 57.4 |
| Ethanol extract | 1.2 g/kg | 2.2 ± 0.8** | 53.2 |

Compared with the model control group, *P < 0.05, **P < 0.01

The results are shown in Table 19. Intragastric administration of 0.2 g/kg and higher doses of *Paliurus ramosissimus* (Lour.) Poir. ethyl acetate extract 3 times can significantly inhibit the degree of pyloric ligation induced gastric ulcers in rats, and the strength of 0.4 g/kg dose group has no significant difference with that of 60 mg/kg ranitidine group; 1.2 g/kg of ethanol, methanol, petroleum ether extracts can also effectively inhibit ulcer degree, suggesting that the four extracts have good anti-ulcer effect.

2. Effect of Ethanol, Methanol, Petroleum Ether Extracts and Ethyl Acetate Extract on 2,4,6-Trinitrotoluene Sulfonic Acid (TNBS) Induced Colitis in Rats Take 90 SD mice, randomly divide into 9 groups with stratification of body weight, namely sham operation group (0.5% mucilage tragacanth), model control group (0.5% mucilage tragacanth), positive control group (dexamethasone), ethyl acetate extract low-dose group, ethyl acetate extract middle-dose group, ethyl acetate extract high-dose group, ethanol extract group, methanol extract group, and petroleum ether extract group. After the animals are fasted for 24 h, perform anesthesia with sodium pentobarbital. Except the sham operation group, perform coloclysis with TNBS and 40% ethanol, and replicate experimental colitis model; 6 h after model construction, administer test substance. At the day 5 of administration, draw tail vein blood and count leukocyte. At day 6, perform urethane anesthesia, draw abdominal aortic blood and sacrifice the animals by cervical dislocation. Cut 9 cm colon from the anus, in an ice bath, cut intestine along the mesenteric edge, wash out the contents, measure the ulcer area, calculate the percentage of ulcer area; weigh the colon, scrap colonic mucosa, and determine tumor necrosis factor (TNF-α) concentration with ELISA method.

TABLE 20

Effect of *Paliurus ramosissimus* (Lour.) Poir. extracts on TNBS induced experimental colitis in rats (n = 10, $\bar{x} \pm s$)

| Group | Dose | Leukocyte count ($10^9$/L) | Ratio of ulcer area (%) | TNF-α (ng/gpro) |
|---|---|---|---|---|
| Sham operation | — | 17.5 ± 1.2** | 5.0 ± 2.3** | 28.1 ± 5.0** |
| Model control | — | 22.9 ± 1.1 | 42.3 ± 13.8 | 234.9 ± 67.3 |
| Positive control (dexamethasone) | 2 mg/kg | 8.4 ± 0.9** | 28.6 ± 10.5* | 73.2 ± 19.6** |
| Ethyl acetate extract low-dose | 0.1 g/kg | 21.5 ± 1.9 | 32.7 ± 12.1 | 189.6 ± 52.7 |
| Ethyl acetate extract middle dose | 0.2 g/kg | 18.6 ± 1.1** | 27.9 ± 15.3* | 137.3 ± 45.9** |
| Ethyl acetate extract high-dose | 0.4 g/kg | 18.2 ± 0.8** | 20.4 ± 9.3** | 102.8 ± 37.5** |
| Methanol extract | 1.2 g/kg | 18.6 ± 0.6** | 18.8 ± 8.0** | 132.7 ± 39.9** |

TABLE 20-continued

Effect of *Paliurus ramosissimus* (Lour.) Poir. extracts on TNBS induced experimental colitis in rats (n = 10, x̄ ± s)

| Group | Dose | Leukocyte count ($10^9$/L) | Ratio of ulcer area (%) | TNF-α (ng/gpro) |
|---|---|---|---|---|
| Petroleum ether extract | 1.2 g/kg | 18.0 ± 0.9** | 25.3 ± 6.8** | 169.0 ± 78.3* |
| Ethanol extract | 1.2 g/kg | 18.5 ± 0.12** | 23.8 ± 10.6** | 121.6 ± 44.0** |

Compared with the model control group, *$P < 0.05$, **$P < 0.01$

The results are shown in Table 21. TNBS induced experimental colitis in rats may manifest as increased inflammatory cells, increased levels of inflammatory cytokines and ulcer on colon surface. 0.2 g/kg and higher doses of *Paliurus ramosissimus* (Lour.) Poir. ethyl acetate extract can inhibit the increase of leukocyte and proinflammatory cytokines TNF-α, and reduce the formation of ulcers; the effect of 1.2 g/kg of ethanol, methanol, petroleum ether extracts is similar to that of ethyl acetate extract, suggesting that the four extracts have good anti-colitis effect.

3. Effect of Ethanol, Methanol, Petroleum Ether Extracts and Ethyl Acetate Extract on Ammonia Induced Chronic Gastritis in Rats Take 120 SD mice, randomly divide into 10 groups with stratification of body weight, namely normal control group (0.5% mucilage tragacanth), model control group (0.5% mucilage tragacanth), positive control group (Sanjiuweitai particle), ethyl acetate extract low-dose group, ethyl acetate extract middle-dose group, ethyl acetate extract high-dose group, ethanol extract group, methanol extract group, and petroleum ether extract group. All animals receive intragastric administration of 0.02% ammonia once daily for 90 consecutive days; meanwhile, animals receive intragastric administration of test substance once daily for 90 consecutive days. On the next day after the last drug administration, sacrifice the animals by cervical dislocation, Take stomach wall of the lesser curvature, fix with 10% formalin, paraffin-embed, slice, HE and PAS stain. On HE staining slice, observe inflammatory reactions and score, and measure mucosal thickness of the gastric body; on PAS staining slice, measure the thickness of positive layer and characteristic mucus layer.

TABLE 21

Effect of *Paliurus ramosissimus* (Lour.) Poir. extracts on ammonia induced experimental chronic gastritis in rats (n = 12, x̄ ± s)

| Group | Dose | Inflammation score | Thickness of mucous layer (mm × $10^{-1}$) | Thickness of mucus layer (mm × $10^{-2}$) |
|---|---|---|---|---|
| Normal control | — | 0.20 ± 0.12** | 5.13 ± 0.62** | 9.60 ± 2.56** |
| Model control | — | 3.23 ± 1.04 | 3.18 ± 0.54 | 3.28 ± 0.69 |
| Positive control (Sanjiuweitai particle) | 0.5 g/kg | 1.56 ± 0.75** | 3.51 ± 0.48 | 6.72 ± 1.93** |
| Ethyl acetate extract low-dose | 0.1 g/kg | 2.07 ± 1.12* | 3.29 ± 0.47 | 6.08 ± 1.71** |
| Ethyl acetate extract middle dose | 0.2 g/kg | 1.62 ± 0.63** | 3.72 ± 0.83 | 7.29 ± 2.05** |
| Ethyl acetate extract high-dose | 0.4 g/kg | 1.08 ± 0.55** | 4.67 ± 1.04** | 7.38 ± 1.36** |
| Combined application | Ethyl acetate extract 0.2 g/kg + Sanjiuweitai 0.5 g/kg | 1.45 ± 0.69** | 4.28 ± 0.61**# | 7.33 ± 1.59** |
| Methanol extract | 1.2 g/kg | 1.58 ± 0.69** | 4.75 ± 1.00** | 7.12 ± 1.15** |
| Petroleum ether extract | 1.2 g/kg | 1.39 ± 0.47** | 4.44 ± 0.86** | 6.33 ± 0.92** |
| Ethanol extract | 1.2 g/kg | 1.28 ± 0.48** | 4.38 ± 0.96** | 7.05 ± 1.14** |

Compared with the model control group, *$P < 0.05$, **$P < 0.01$;
Compared with the positive control group (Sanjiuweitai particle group), #$P < 0.05$ The results are shown in Table 21. For ammonia induced experimental chronic gastritis, *Paliurus ramosissimus* (Lour.) Poir. ethyl acetate extract has effects in inhibiting inflammation and increasing layer thickness of mucous layer and mucus layer, especially in inhibiting inflammation and increasing thickness of mucus layer; the effect of 1.2 g/kg of ethanol, methanol, petroleum ether extracts is similar to that of ethyl acetate extract, suggesting that the four extracts have good effect against chronic gastritis.

4. Effect of Ethyl Acetate Extract in Combination of Sanjiuweitai on Pylorus Ligation Induced Experimental Gastric Ulcer in Rats Take 50 SD mice, randomly divide into 5 groups with stratification of body weight, namely model control group (0.5% mucilage tragacanth), positive control group (ranitidine), ethyl acetate extract group, Sanjiuweitai particle group and combined application group. In all groups, mice receive test substance via intragastric administration once a day for 3 consecutive days. 1 h after the last administration, perform pylorus ligation, 15 hours after the surgery, sacrifice the animals by cervical dislocation, take out the stomach, fix with 1% formaldehyde for 20 min, then dissect, observe the extent of mucosal damage by stereoscopic microscope, and calculate ulcer index and ulcer inhibition rate.

TABLE 22

Effect of ethyl acetate extract in combination of Sanjiuweitai on pylorus ligation induced experimental gastric ulcer in rats (n = 10, $\bar{x} \pm s$)

| Group | Dose | Ulcer index | Ulcer inhibition rate (%) |
|---|---|---|---|
| Model control | — | 4.5 ± 1.3 | — |
| Positive control (ranitidine) | 60 mg/kg | 1.8 ± 0.6** | 60.0 |
| Ethyl acetate extract | 0.2 g/kg | 3.0 ± 0.9* | 33.3 |
| Sanjiuweitai particle | 1 g/kg | 4.2 ± 1.7 | 6.7 |
| Combined application | Ethyl acetate extract 0.2 g/kg + Sanjiuweitai 1 g/kg | 2.7 ± 1.1**## | 40.0 |

Compared with the model control group, *P < 0.05, **P < 0.01;
Compared with the Sanjiuweitai particle group, #P < 0.05, ##P < 0.01.

The results are shown in Table 22. The intragastric administration of 0.2 g/kg *Paliurus ramosissimus* (Lour.) Poir. ethyl acetate extract three times can significantly inhibit the degree of pyloric ligation induced gastric ulcers in rats; Sanjiuweitai alone does not have effect in the model, but when being applied in combination with the extract of the present invention, it can significantly enhance the efficacy of anti-ulcer, suggesting that it has synergistic effect with anti-ulcer drugs or drug combinations.

5. Effect of Ethyl Acetate Extract in Combination of Sanjiuweitai on Ammonia Induced Experimental Chronic Gastritis in Rats This experiment is carried out with pharmacodynamics experiment 2, and the results showed in Table 21, with shared normal control group and model control group. The results have showed that Sanjiuweitai can significantly increase mucus layer thickness, reduce inflammation, but does not have significant effect on mucous layer thickness. And the combination with the extract of the present invention can enhance the effects by Sanjiuweitai and also effectively increase mucous layer thickness, suggesting that it has synergistic effect with chronic gastritis drugs or drug combinations.

In summary, *Paliurus ramosissimus* (Lour.) Poir. extract and the raw medicine material, *Paliurus ramosissimus* (Lour.) Poir., have significant anti-tumor activity, antifungal activity, anti-fibrotic activity and, bi-directional immunomodulatory effects, as well as the effects in treatment of oral and gastrointestinal inflammation or/and ulcer.

We claim:

1. A method for treating a tumor in a subject, said method comprising administering to the subject in need thereof a composition comprising *Paliurus ramosissimus*, wherein the *Paliurus ramosissimus* is a *Paliurus ramosissimus* fresh leaf ethanolic extract or a *Paliurus ramosissimus* whole plant ethanolic extract.

2. The method according to claim 1, wherein the composition comprising *Paliurus ramosissimus* is a pharmaceutical composition comprising a *Paliurus ramosissimus* fresh leaf ethanolic extract or a *Paliurus ramosissimus* whole plant ethanolic extract as the active ingredient, and further comprising a pharmaceutically acceptable carrier.

* * * * *